United States Patent
Huang et al.

(10) Patent No.: US 9,315,513 B2
(45) Date of Patent: Apr. 19, 2016

(54) BENZIMIDAZOLE DERIVATIVES AND THEIR PHARMACEUTICAL COMPOSITIONS AND USES

(75) Inventors: Zhenhua Huang, Shandong (CN); Guanglian Zhou, Shandong (CN)

(73) Assignee: XUANZHU PHARMA CO., LTD., Jinan, Shandong (CN)

( * ) Notice: Subject to any disclaimer, the term of this patent is extended or adjusted under 35 U.S.C. 154(b) by 456 days.

(21) Appl. No.: 13/576,903

(22) PCT Filed: Jan. 31, 2011

(86) PCT No.: PCT/CN2011/000181
§ 371 (c)(1),
(2), (4) Date: Oct. 3, 2012

(87) PCT Pub. No.: WO2011/095057
PCT Pub. Date: Aug. 11, 2011

(65) Prior Publication Data
US 2013/0023568 A1     Jan. 24, 2013

(30) Foreign Application Priority Data
Feb. 2, 2010 (CN) .......................... 2010 1 0104455

(51) Int. Cl.
*C07D 491/048* (2006.01)
*C07D 487/04* (2006.01)
*C07D 491/052* (2006.01)
*C07D 491/056* (2006.01)

(52) U.S. Cl.
CPC .......... *C07D 491/048* (2013.01); *C07D 487/04* (2013.01); *C07D 491/052* (2013.01); *C07D 491/056* (2013.01)

(58) Field of Classification Search
CPC ............. C07D 487/04; C07D 491/048; C07D 491/052; C07D 491/056
See application file for complete search history.

(56) References Cited

U.S. PATENT DOCUMENTS

| | | |
|---|---|---|
| 4,255,431 A | 3/1981 | Junggren et al. |
| 4,560,693 A | 12/1985 | Rainer |
| 4,599,347 A | 7/1986 | Krassó et al. |
| 4,730,003 A | 3/1988 | von der Saal et al. |
| 4,758,579 A | 7/1988 | Kohl et al. |
| 5,039,806 A | 8/1991 | Brändsträm et al. |
| 5,167,695 A | 12/1992 | Brill et al. |
| 5,661,147 A | 8/1997 | Machii et al. |
| 7,019,147 B1 | 3/2006 | Barth et al. |

FOREIGN PATENT DOCUMENTS

| | | |
|---|---|---|
| CN | 1402721 A | 3/2003 |
| EP | 0127763 A1 | 12/1984 |
| EP | 0166287 A1 | 1/1986 |
| EP | 0214592 A2 | 3/1987 |
| EP | 0268956 A2 | 6/1988 |
| EP | 0401582 B1 | 7/1994 |
| GB | 2082580 A | 3/1982 |
| GB | 2174988 A | 11/1986 |
| JP | S 57-70886 A | 5/1982 |
| JP | S 59-181277 A | 10/1984 |
| JP | S 59-206386 A | 11/1984 |
| JP | S 61-22079 A | 1/1986 |
| JP | S 62-59279 A | 3/1987 |
| JP | 62-145083 A | 6/1987 |
| JP | H 03-95180 A | 4/1991 |
| JP | 3-161440 A | 7/1991 |
| JP | 2003-515603 A | 5/2003 |

OTHER PUBLICATIONS

English language abstract not available for CN 1402721; however, see English language equivalent U.S. Pat. No. 7,019,147. Original Document extracted from the espacenet.com database on Sep. 26, 2012, 222 pages.
English language abstract for EP 0401582 extracted from the espacenet.com database on Sep. 26, 2012, 31 pages.
European Search Report for Application EP 11739336 dated Aug. 16, 2013, 18 pages.
Camilleri, Patrick et al., "Chiral Chromatography and Multivariate Quantitative Structure-Property Relationships of Benzimidazole Suplhoxides", Journal of Computer-Aided Molecular Design, vol. 7, Oct. 1992, 9 pages.
Cereda, Enzo et al., "Anti-Secretory and Anti-Ulcer Activities of Some New 2-(2-Pyridylniethyl-Sulfinyl)-Benzimidazoles", Original Paper, Eur. J. Med. Chem., vol. 22, Jun. 1987, 11 pages.
Kohl, Bernard, et al., "(H+,K+)-ATPase Inhibiting 2-[(2-Pyridylmethyl)sulfinyl]benzimidazoles. A Novel Series of Dimethoxypyridyl-Substituted Inhibitors with Enhanced Selectivity. The Selection of Pantoprazole as a Clinical Candidate", J. Med. Chem., vol. 35, Jul. 1991, 9 pages.

(Continued)

*Primary Examiner* — Shengjun Wang
*Assistant Examiner* — Jody Karol
(74) *Attorney, Agent, or Firm* — Howard & Howard Attorneys PLLC

(57) ABSTRACT

The present invention relates to benzimidazole derivatives and their pharmaceutical compositions and uses, specifically to benzimidazole derivatives of Formula (I), or their stereoisomer, pharmaceutically acceptable salt or solvates thereof, in which $R^1$, $R^2$, $R^3$, $R^4$, $R^5$ and n have the definitions in the description; the present invention further relates to a pharmaceutical composition containing the compounds, methods for preparing the compounds, and use of the compounds for manufacturing of a medicament for prophylaxis and/or treatment of peptic ulcer, ulcer hemorrhage and diseases associated with gastric acid.

(I)

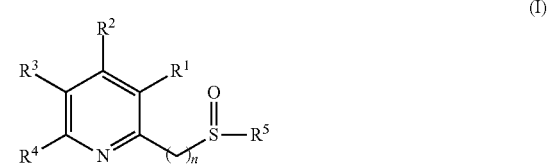

13 Claims, No Drawings

(56) References Cited

OTHER PUBLICATIONS

Rodgers, Gary R., et al., "Linear Expanded Xanthines [1]", Department of Pharmacology, University of Sheffield, Western Bank, Sheffield S102TN England, Monatshefte fur Chemie, vol. 117, 1986, 4 pages.
Database CA [Online] Chemical Abstracts Service, Columbus, Ohio, US; 1987, "Preparation of fused imidazole derivatives as antiulcer agents", XP002708075, Database accession No. 1987:636707, Jun. 29, 1987, 1 page.
Database CA [Online] Chemical Abstracts Service, Columbus, Ohio, US; 1991, "Hiroshi M., et al., Medical bactericides containing condenzed imidazole derivatives", XP002708076, Database accession No. 1991:639753, Jul. 11, 1991, 2 pages.
Database CA [Online] Chemical Abstracts Service, Columbus, Ohio, US; XP002708077, Database accession No. 491866-49-0, Feb. 19, 2003, 1 page.
Database CA [Online] Chemical Abstracts Service, Columbus, Ohio, US; XP002708078, Database accession No. 1023812-42-1, May 30, 2008, 1 page.
Database CA [Online] Chemical Abstracts Service, Columbus, Ohio, US; XP002708079, Database accession No. 929338-72-7, Apr. 8, 2007, 1 page.
Database CA [Online] Chemical Abstracts Service, Columbus, Ohio, US; XP002708080, Database accession No. 929338-68-1, Apr. 8, 2007, 1 page.
Database CA [Online] Chemical Abstracts Service, Columbus, Ohio, US; XP002708081, Database accession No. 929338-66-9, Apr. 8, 2007, 1 page.
Database CA [Online] Chemical Abstracts Service, Columbus, Ohio, US; XP002708082, Database accession No. 491866-49-0, Feb. 19, 2003, 1 page.
English language abstract for EP 0127763 extracted from espacenet.com database on Apr. 28, 2014, 50 pages.
English language abstract for EP 0166287 extracted from espacenet.com database on Apr. 28, 2014, 69 pages.
English language abstract for EP 0214592 extracted from espacenet.com database on Apr. 28, 2014, 55 pages.
Surender et al., "Synthesis and Biological Activity of 2-Mercapto-1H-Imidazo[4,5-f]Quinoline Derivatives",Phosphorus, Sulfur, and Silicon and the Related Elements, 35: 3 (1988) pp. 267-271.
Rao et al., "Heterocyclic Systems Containingbridge Head Nitrogen Atom: Reaction of 5-Mercapto-4H-Imidazo[4,5-e]-[2,1,3]Benzothiadiazoles and 5,6-Diamino[2,1,3]Benzothiazole With 3-(2-Bromoacetyl)Coumarins", Phosphorus, Sulfur, and Silicon and the Related Elements, 179: 10, (2004), pp. 2105-2111.
Ronne et al., "Synthetic Routes to the Carcinogen IQ and Related 3H-Imidazo[4,5-F]Quinolines", Acta Chemica Scandinavica, 48 (1994), pp. 823-830.
English language abstract not found for JPS 57-70886; however, see English language equivalent U.S. 4,599,347. Original document extracted from espacenet.com database on Oct. 30, 2014, 25 pages.
English language abstract not found for JPS 59-181277; however, see English language equivalent U.S. Pat. No. 5,039,806. Original document extracted from espacenet.com database on Oct. 30, 2014, 51 pages.
English language abstract not found for JPS 59-206386; however, see English language equivalent U.S. Pat. No. 4,560,693 (previously submitted on May 1, 2014). Original document extracted from espacenet.com database on Oct. 30, 2014, 51 pages.
English language abstract not found for JPS 61-22079; however, see partial English language translation/statement of relevance for JPS 61-22079 provided by CCPIT Patent and Trademark Law Office on Nov. 24, 2014, 1 page.
English language abstract not found for JPS 62-59279; however, see English language equivalent U.S. 4,730,003 (previously submitted on May 1, 2014). Original document extracted from PAJ database on Oct. 30, 2014, 26 pages.
English language abstract not found for JPH 03-95180; however, see English language equivalent U.S. 5,167,695 (previously submitted on Feb. 7, 2013). Original document extracted from espacenet.com database on Oct. 30, 2014, 16 pages.
English language abstract not found for JP 2003-515603; however, see English language equivalent U.S. 7,019,147 (previously submitted on Feb. 7, 2013). Original document extracted from espacenet.com database on Oct. 30, 2014, 272 pages.
English language Abstract/Statement of Relevancy for Fridman et al., "Condensation of O-Diamino Derivatives of 2-Methylbenzothiazole With Carboxylic Acids. II. Thiazolobenzimidazoles", Zhurnal Obshchei Khimii, 30 (1960), pp. 1520-1526, provided by CCPIT Patent and Trademark Law Office on Nov. 24, 2014, 1 page. Original foreign language document previously provided on Apr. 12, 2013, and again provided herein for convenience.
English language Abstract/Statement of Relevancy for Il'Ina et al., "Synthesis of Some Thionoimidazole Structures of Quinoline and Indole Series", Khimiya Geterotsiklicheskikh Soedinenii, 8 (1973), pp. 1112-1114, provided by CCPIT Patent and Trademark Law Office on Nov. 24, 2014, 1 page. Original foreign language document previously provided on Apr. 12, 2013, and again provided herein for convenience.
Wuts and Greene, Greene's Protective Groups in Organic Synthesis, Fourth Edition, 2007, pp. 431-532.
English language abstract for JP 3-161440 extracted from the espacenet.com database on Sep. 26, 2012, 6 pages.
English language abstract for JP 62-145083 extracted from the espacenet.com database on Sep. 26, 2012, 6 pages.
International Search Report for Application No. PCT/CN2011/000181 dated May 5, 2011, 14 pages.

BENZIMIDAZOLE DERIVATIVES AND THEIR PHARMACEUTICAL COMPOSITIONS AND USES

RELATED APPLICATIONS

This application is the National Stage of International Patent Application No. PCT/CN2011/000181, filed on Jan. 31, 2011, which claims priority to and all the advantages of Chinese Patent Application No. CN 201010104455.X, filed on Feb. 2, 2010.

TECHNICAL FIELD

The present invention belongs to the technical field of pharmaceutical compounds, and specifically relates to benzimidazole derivatives, stereoisomers, solvates or pharmaceutically acceptable salts thereof. The present invention also relates to pharmaceutical compositions comprising these compounds, methods for preparing these compounds, and uses of these compounds in the manufacture of medicaments for prophylaxis and/or treatment of peptic ulcer, ulcer bleeding and diseases associated with gastric acid.

BACKGROUND

Diseases of digestive system are frequently encountering diseases, in which the incidence rate of peptic ulcer is 10-12% relative to the total population. Gastric acid is the main reason for the peptic ulcer. The preliminary treatment methods mainly comprise of antacids (such as sodium bicarbonate, aluminum hydroxide, etc.) to neutralize gastric acid to alleviate symptoms. Since the 1970s, the discovery of gastric acid secretion inhibitors such as $H_2$ receptor blocking agents, proton pump inhibitors, etc. brings a new era of peptic ulcer treatment. These drugs induce irreversible inhibition of $H^+$, $K^+$-ATP enzymes of secretory microtubules constituting parietal cell top membrane and tubular bubbles in cytoplasm, thereby effectively inhibiting gastric secretion, and thus they have merits of quick onset and high ulcer healing rate that can significantly reduce surgery rate.

U.S. Pat. No. 4,255,431 discloses a compound of Formula A, i.e., Omeprazole.

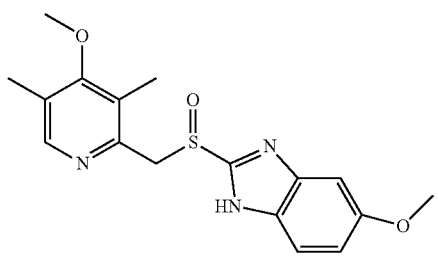

(A)

Omeprazole is the first marketed proton pump inhibitor, and gradually prevailed in competition with $H_2$ receptor antagonist in antiulcer drug market, becomes the first best-selling drug in 1996 due to its unique therapeutic effect, and at the top of list for several consecutive years. Following Omeprazole, many new proton pump inhibitors are continuously marketed, including Lansoprazole, Pantoprazole, Rabeprazole and Esomeprazole.

Patent EP0268956 discloses a compound of Formula B, i.e., Rabeprazole.

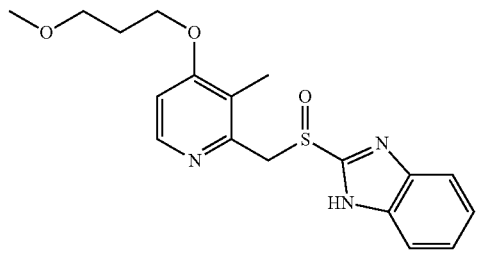

(B)

Rabeprazole was marketed in Japan in 1997, and China in 2001, which has an activity against gastric acid secretion in vitro 2-10 times that of Omeprazole, and more quick and significant therapeutically effects. Rabeprazole can be quickly activated, and achieve the maximum acid inhibition effect within 5 min, but its duration of action is shorter than that of Omeprazole.

GB2174988 discloses the following compound 81:

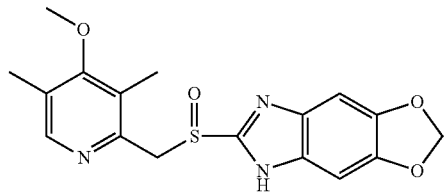 [SMILES: COc1c(C)cnc(CS(=O)c2nc3cc4c(cc3[nH]2)OCO4)c1C]

However, proton pump inhibitors have a relatively long time to achieve the strongest effect, the maximum acid inhibition effect can only be achieved after 3-5 days at therapeutically dose, and these drugs may have significant interaction with other drugs, and great individual difference in pharmacokinetics.

Hence, it is still in need to develop new proton pump inhibitors that have quick onset of action, good acid inhibition effect, less interaction with other drugs and small individual difference.

DESCRIPTION OF THE INVENTION

The inventors find a group of proton pump inhibitors via a devil of experiments, and they have good inhibition effect to gastric acid secretion.

In one aspect, the present invention provides a compound of Formula (I), or a stereoisomer, solvate or pharmaceutically acceptable salt thereof:

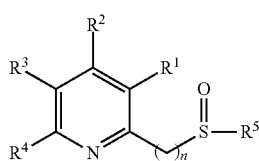

(I)

in which, $R^1$, $R^2$, $R^3$ and $R^4$ are independently hydrogen atom, $C_{1-6}$ alkyl, $C_{1-6}$ alkoxyl, $C_{1-6}$ alkoxyl-$C_{1-6}$ alkyl, $C_{1-6}$ alkoxyl-$C_{1-6}$ alkoxyl, halo$C_{1-6}$ alkyl, halo$C_{1-6}$ alkoxyl, $C_{1-6}$ alkylamino, di($C_{1-6}$ alkyl)amino, $C_{1-6}$ alkylcarbonyl, $C_{1-6}$ alkylcarbonyloxy, $C_{1-6}$alkyloxycarbonyl, phenyl, phenyl-$C_{1-6}$ alkyl, phenyl-$C_{1-6}$ alkoxyl or phenoxy;

$R^5$ represents formula

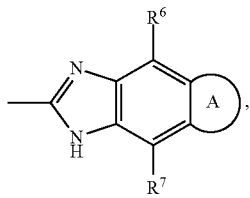

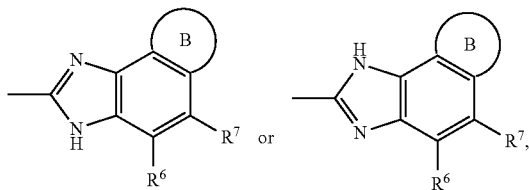

$R^6$ and $R^7$ are independently hydrogen atom, halogen atom, $C_{1-6}$ alkyl, $C_{1-6}$ alkoxyl, $C_{1-6}$ alkoxyl-$C_{1-6}$ alkyl, $C_{1-6}$ alkoxyl-$C_{1-6}$ alkoxyl, halo$C_{1-6}$ alkyl, halo$C_{1-6}$ alkoxyl, $C_{1-6}$ alkylamino, di($C_{1-6}$ alkyl)amino, hydroxyl, hydroxyl-$C_{1-6}$ alkyl, carboxyl, carboxyl-$C_{1-6}$ alkyl, amino, amino-$C_{1-6}$ alkyl, $C_{1-6}$ alkylcarbonyl, $C_{1-6}$ alkylcarbonyloxy, $C_{1-6}$ alkyloxycarbonyl, aminosulfonyl, carbamoyl or $C_{1-6}$ alkylcarbamoyl, Ring A and ring B are independently 5- to 7-membered monocycle having 1-3 oxygen atoms, sulfur atoms and/or nitrogen atoms, and the monocycle can be optionally substituted with 1-4 $R^8$, $R^8$ is hydrogen atom, halogen atom, $C_{1-6}$ alkyl, $C_{1-6}$ alkoxyl, $C_{1-6}$ alkoxyl-$C_{1-6}$ alkyl, $C_{1-6}$ alkoxyl-$C_{1-6}$ alkoxyl, halo$C_{1-6}$ alkyl, halo$C_{1-6}$ alkoxyl, $C_{1-6}$ alkylamino, di($C_{1-6}$ alkyl)amino, hydroxyl, hydroxyl-$C_{1-6}$ alkyl, carboxyl, carboxyl-$C_{1-6}$ alkyl, amino, amino-$C_{1-6}$ alkyl, $C_{1-6}$ alkyl-carbonyl, $C_{1-6}$ alkyl-carbonyloxy, $C_{1-6}$ alkyl-oxycarbonyl, aminosulfonyl, carbamoyl, $C_{1-6}$ alkyl-carbamoyl or $C_{1-6}$ alkylformylamino, and n is 1 or 2, with the proviso that ring A is not

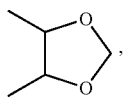

with the proviso that when ring A is

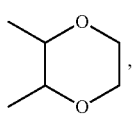

$R^8$ is not a halogen atom.

In one embodiment of this aspect, the compound of the present invention is a compound of Formula (I), or a stereoisomer, solvate or pharmaceutically acceptable salt thereof:

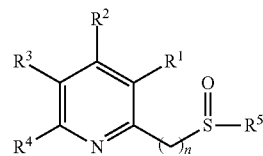

in which, $R^1$, $R^2$ and $R^3$ are independently hydrogen atom, $C_{1-4}$ alkyl, $C_{1-4}$ alkoxyl, $C_{1-4}$ alkoxyl-$C_{1-4}$ alkyl, $C_{1-4}$ alkoxyl-$C_{1-4}$ alkoxyl, halo$C_{1-4}$ alkyl or halo$C_{1-4}$ alkoxyl;

$R^4$ is hydrogen atom;

$R^5$ represents formula

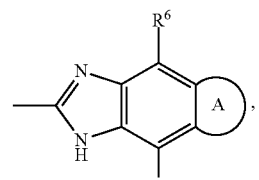

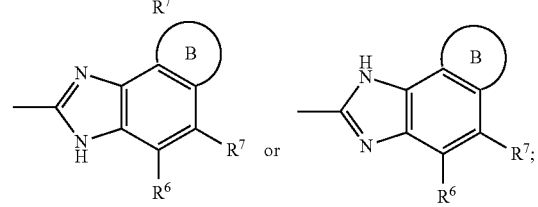

$R^6$ and $R^7$ are independently hydrogen atom, fluorine atom, chlorine atom, $C_{1-4}$ alkyl, $C_{1-4}$ alkoxyl, $C_{1-4}$ alkoxyl-$C_{1-4}$ alkoxyl, fluoro-$C_{1-4}$ alkyl, fluoro-$C_{1-4}$ alkoxyl, $C_{1-4}$ alkylamino, di($C_{1-4}$ alkyl)amino, hydroxyl, carboxyl, amino, aminosulfonyl, carbamoyl or $C_{1-4}$ alkyl-carbamoyl, Ring A and ring B are independently 5- to 7-membered monocycle having 1-2 oxygen atoms, sulfur atoms and/or nitrogen atoms, and the monocycle can be optionally substituted with 1-2 $R^8$, $R^8$ is hydrogen atom, fluorine atom, chlorine atom, $C_{1-4}$ alkyl, $C_{1-4}$ alkoxyl, $C_{1-4}$ alkoxyl-$C_{1-4}$ alkyl, $C_{1-4}$ alkoxyl-$C_{1-4}$ alkoxyl, fluoro-$C_{1-4}$ alkyl or fluoro-$C_{1-4}$ alkoxyl, and n is 1, with the proviso that ring A is not

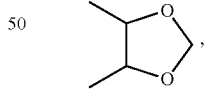

with the proviso that when ring A is

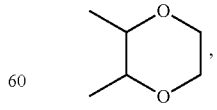

$R^8$ is not a halogen atom.

In another embodiment of this aspect, the compound of the present invention is a compound of Formula (I), or a stereoisomer, solvate or pharmaceutically acceptable salt thereof, in which $R^1$, $R^2$ and $R^3$ are independently hydrogen atom, $C_{1-4}$ alkyl, $C_{1-4}$ alkoxyl, $C_{1-4}$alkoxyl-$C_{1-4}$ alkyl, $C_{1-4}$alkoxyl-$C_{1-4}$ alkoxyl, halo$C_{1-4}$ alkyl or halo$C_{1-4}$ alkoxyl;

$R^4$ is hydrogen atom;

$R^5$ represents formula

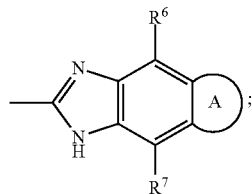

$R^6$ and $R^7$ are independently hydrogen atom;

Ring A is a 5-membered ring having one oxygen atom, and n is 1.

In another one embodiment of this aspect, the compound of the present invention is a compound of Formula (I), or a stereoisomer, solvate or pharmaceutically acceptable salt thereof, in which, $R^1$ is $C_{1-4}$ alkyl or halo$C_{1-4}$ alkyl;

$R^2$ is $C_{1-4}$ alkoxyl, $C_{1-4}$alkoxyl-$C_{1-4}$ alkyl, $C_{1-4}$alkoxyl-$C_{1-4}$ alkoxyl or halo$C_{1-4}$ alkoxyl;

$R^3$ and $R^4$ are independently hydrogen atom;

$R^5$ represents formula

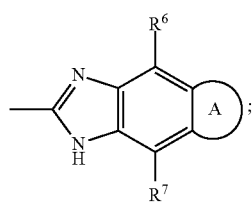

$R^6$ and $R^7$ are independently hydrogen atom;

Ring A is a 5-membered ring having one oxygen atom, and n is 1.

In another one embodiment of the aspect, the compound of the present invention is a compound of Formula (I), or a stereoisomer, solvate or pharmaceutically acceptable salt thereof:

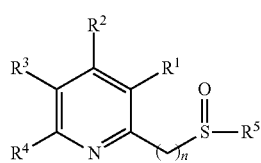

(I)

in which, $R^1$, $R^2$ and $R^3$ are independently hydrogen atom, methyl, ethyl, methoxyl, ethoxyl, methoxylmethoxyl, 2-methoxylethoxyl, 3-methoxylpropoxy, ethoxylmethoxyl, 2-ethoxylethoxyl, 3-ethoxylpropoxy, propoxymethoxyl, methoxylmethyl, 2-methoxylethyl, 3-methoxylpropyl, ethoxylmethyl, 2-ethoxylethyl, 3-ethoxylpropyl, propoxymethyl, fluoromethyl, difluoromethyl, trifluoromethyl, fluoromethoxyl, difluoromethoxyl, trifluoromethoxyl, 2,2-difluoroethoxyl or 2,2,2-trifluoroethoxyl;

$R^4$ is hydrogen atom;

$R^5$ represents

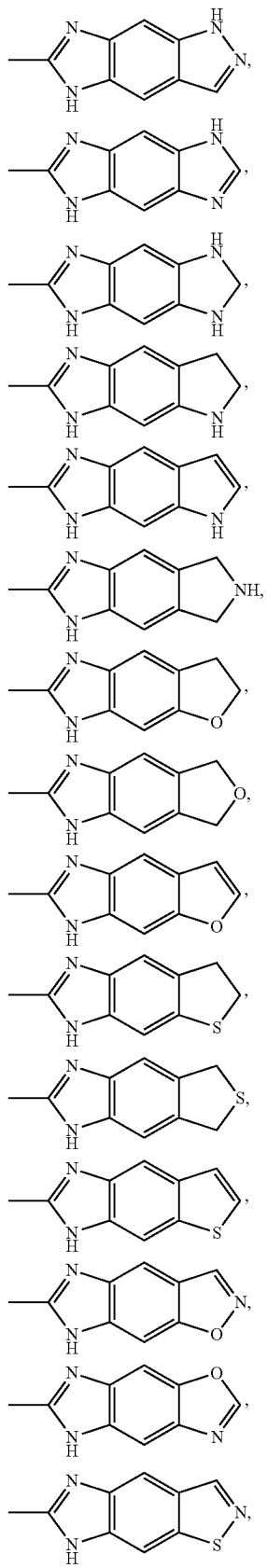

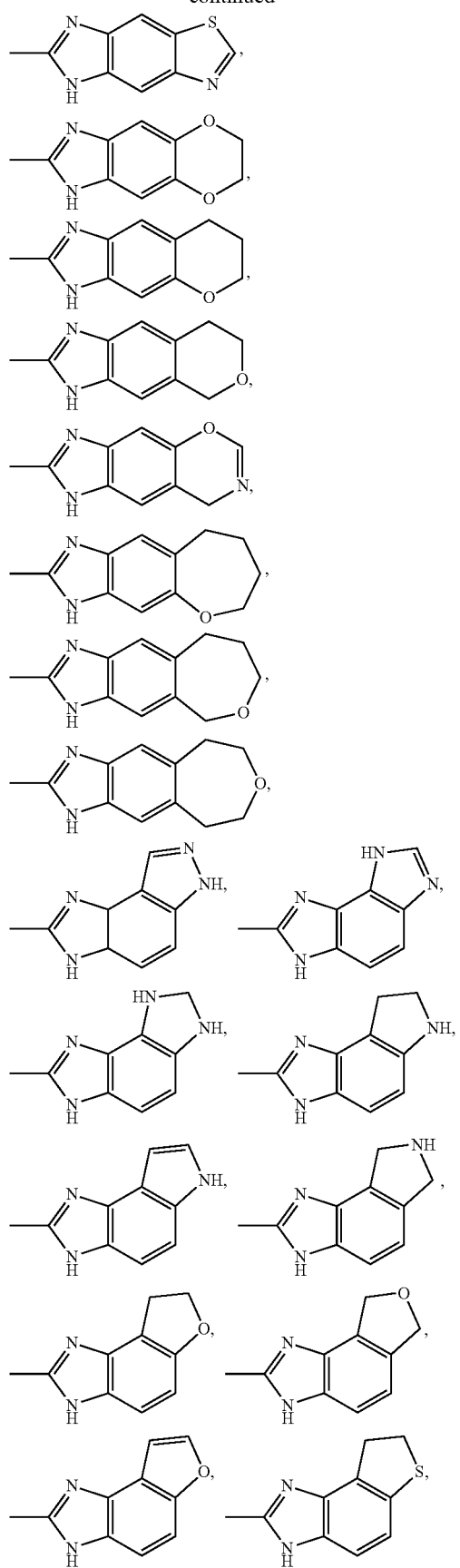
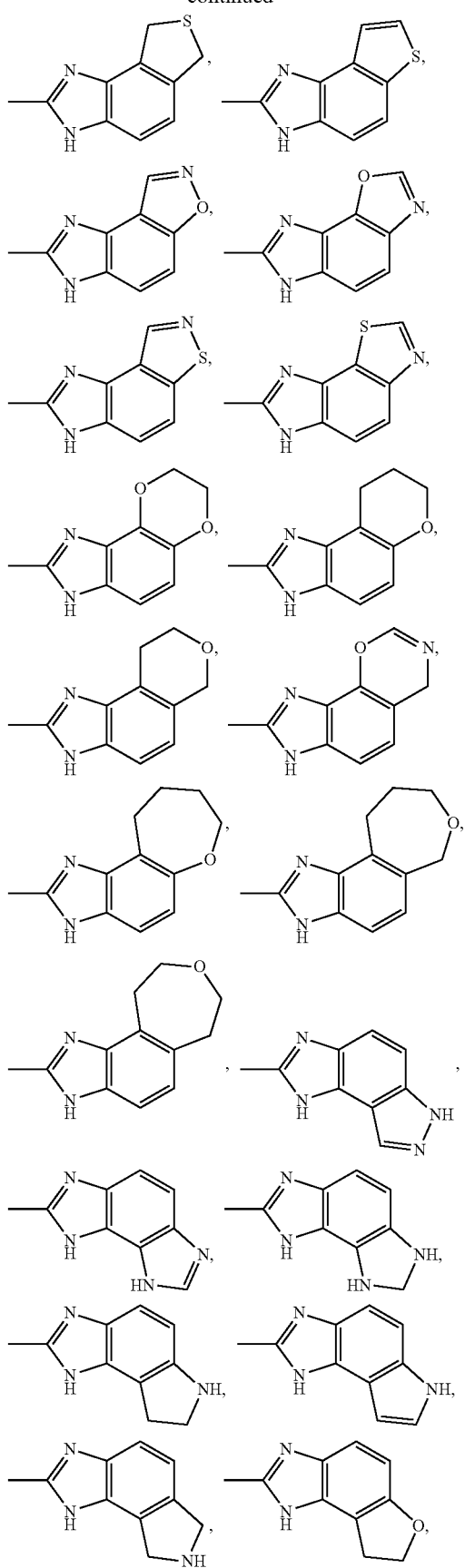

-continued

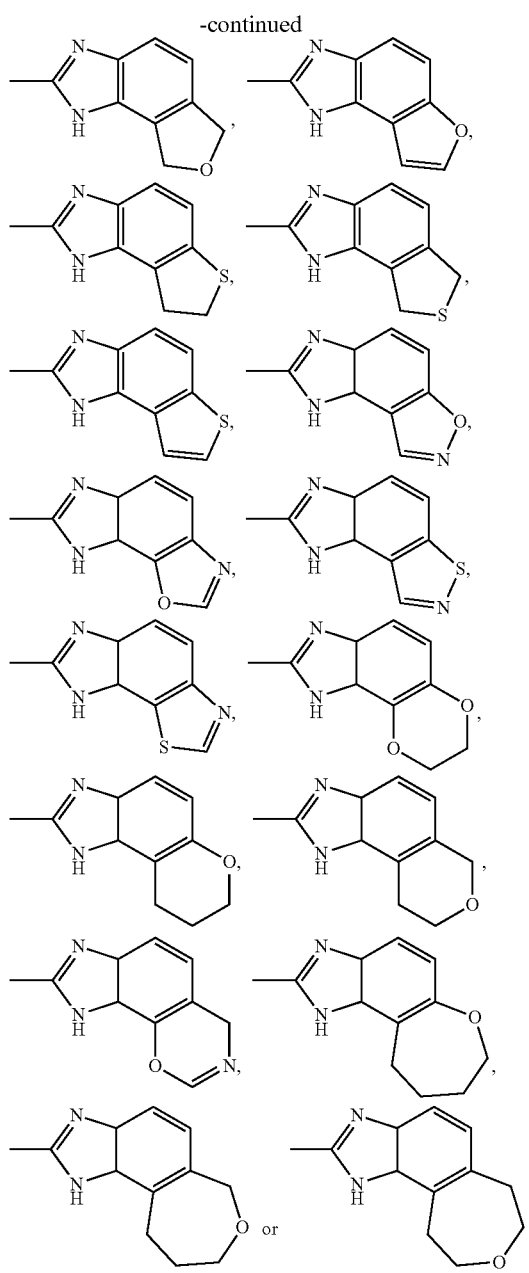

and
n is 1.

In another embodiment of this aspect, the compound of the present invention is a compound of Formula (I), or a stereoisomer, solvate or pharmaceutically acceptable salt thereof:

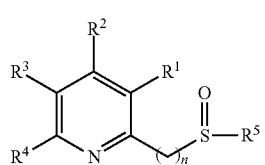
(I)

in which, $R^1$, $R^2$ and $R^3$ are independently hydrogen atom, methyl, ethyl, methoxyl, ethoxyl, methoxylmethoxyl, 2-methoxylethoxyl, 3-methoxylpropoxy, ethoxylmethoxyl, 2-ethoxylethoxyl, 3-ethoxylpropoxy, propoxymethoxyl, difluoromethyl, trifluoromethyl, difluoromethoxyl, trifluoromethoxyl, 2,2-difluoroethoxyl or 2,2,2-trifluoroethoxyl;

$R^4$ is hydrogen atom;

$R^5$ represents

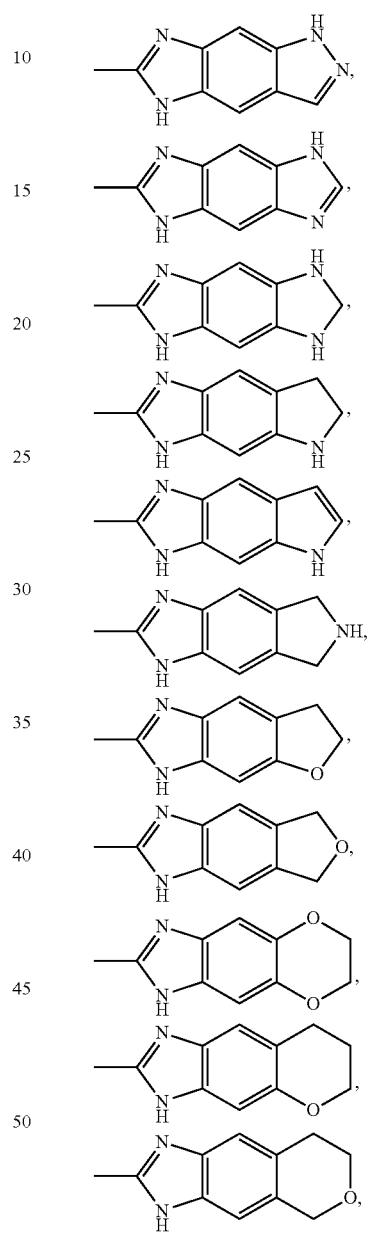

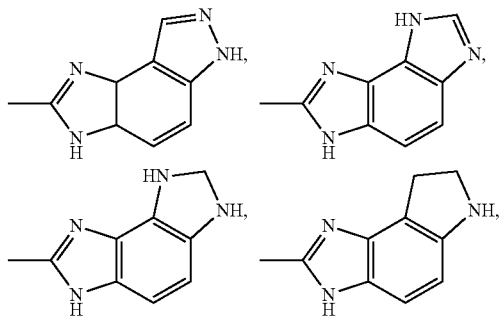

-continued

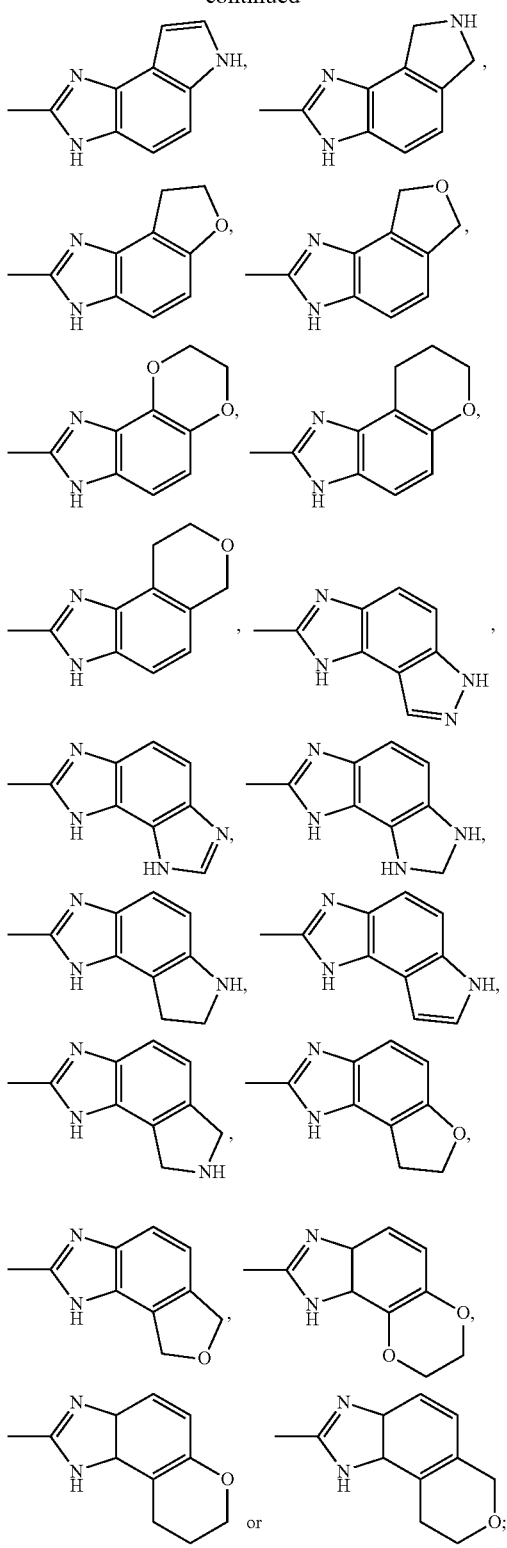

and
n is 1.

In another embodiment of this aspect, the compound of the present invention is a compound of Formula (I), or a stereoisomer, solvate or pharmaceutically acceptable salt thereof:

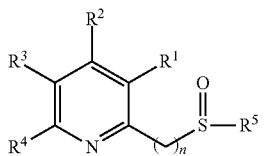

in which, $R^1$ is hydrogen atom, methyl or methoxyl;

$R^2$ is methoxyl, 3-methoxylpropoxy or 2,2,2-trifluoroethoxyl;

$R^3$ is hydrogen atom, methyl or methoxyl;

$R^4$ is hydrogen atom;

$R^5$ represents

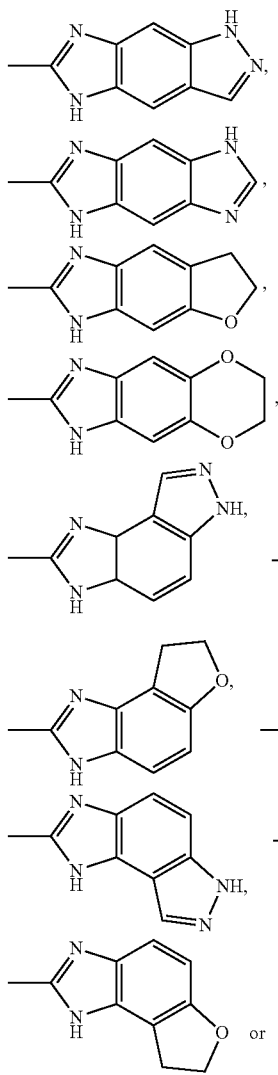

and
n is 1.

In another embodiment of this aspect, the compound of the present invention is a compound of Formula (I), or a stereoisomer, solvate or pharmaceutically acceptable salt thereof:

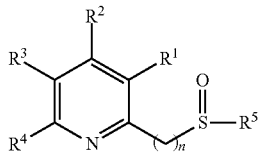

(I)

in which, $R^1$ is methyl or methoxyl;
$R^2$ is methoxyl, 3-methoxylpropoxy or 2,2,2-trifluoroethoxyl;
$R^3$ is hydrogen atom or methyl;
$R^4$ is hydrogen atom;
$R^5$ represents

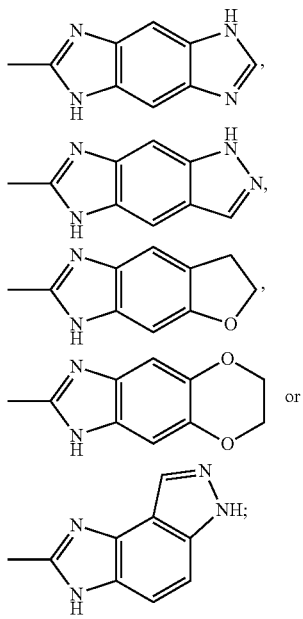

and
n is 1.

In another embodiment of this aspect, the compound of the present invention has a structure of the following formula:

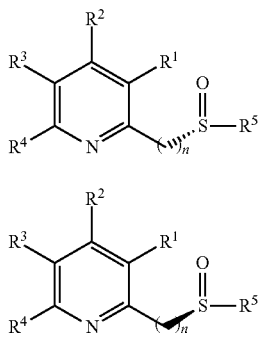

(I-1)

(I-2)

in which,
$R^1$, $R^2$ and $R^3$ are independently hydrogen atom, $C_{1-4}$ alkyl, $C_{1-4}$ alkoxyl, $C_{1-4}$alkoxyl-$C_{1-4}$ alkyl, $C_{1-4}$alkoxyl-$C_{1-4}$ alkoxyl, halo$C_{1-4}$ alkyl or halo$C_{1-4}$ alkoxyl;
$R^4$ is hydrogen atom;
$R^5$ represents formula

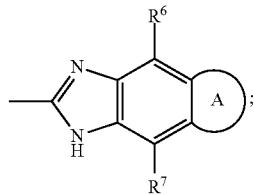

$R^6$ and $R^7$ are independently hydrogen atom;
Ring A is a 5-membered ring having one oxygen atom, and n is 1.

In another embodiment of this aspect, the compound of the present invention has a structure of the following formula:

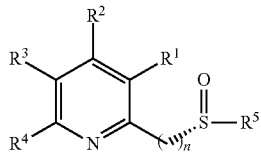

(I-1)

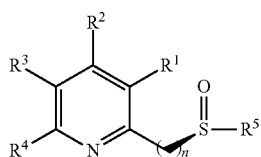

(I-2)

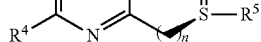

in which,
$R^1$ is $C_{1-4}$ alkyl or halo$C_{1-4}$ alkyl;
$R^2$ is $C_{1-4}$ alkoxyl, $C_{1-4}$ alkoxyl-$C_{1-4}$ alkyl, $C_{1-4}$alkoxyl-$C_{1-4}$ alkoxyl or halo$C_{1-4}$ alkoxyl;
$R^3$ and $R^4$ are independently hydrogen atom;
$R^5$ represents formula

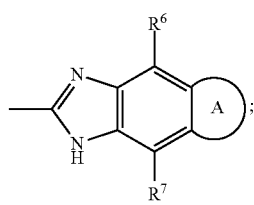

$R^6$ and $R^7$ are independently hydrogen atom;
Ring A is a 5-membered ring having one oxygen atom, and n is 1.

In another embodiment of this aspect, the compound of the present invention is:
(S)-2-[[[4-(3-methoxylpropoxy)-3-methyl-2-pyridyl]methyl]sulfinyl]-6,7-dihydro-3H-benzofuro[5,6-d]imidazole, or
(R)-2-[[[4-(3-methoxylpropoxy)-3-methyl-2-pyridyl]methyl]sulfinyl]-6,7-dihydro-3H-benzofuro[5,6-d]imidazole, or
a pharmaceutically acceptable salt thereof.

TABLE 1

Part of compounds of the present invention

| No. | Structural formula | Chemical name |
|---|---|---|
| 1 | | 2-[[4-(3-methoxylpropoxy)-3-methylpyridin-2-yl]methylsulfinyl]-6,7-dihydro-3H-benzofuro[5,6-d]imidazole |
| 2 | | 2-[(4-methoxyl-3,5-dimethylpyridin-2-yl)methylsulfinyl]-6,7-dihydro-3H-benzofuro[5,6-d]imidazole |
| 3 | | 2-[[3-methyl-4-(2,2,2-trifluoroethoxyl)pyridin-2-yl]methylsulfinyl]-6,7-dihydro-3H-benzofuro[5,6-d]imidazole |
| 4 | | 2-[(3,4-dimethoxylpyridin-2-yl)methylsulfinyl]-6,7-dihydro-3H-benzofuro[5,6-d]imidazole |
| 5 | | 2-[[4-(3-methoxylpropoxy)-3-methylpyridin-2-yl]methylsulfinyl]-3,6-dihydro-imidazo[4,5-e]indazole |

TABLE 1-continued

Part of compounds of the present invention

| No. | Structural formula | Chemical name |
|---|---|---|
| 6 | | 2-[[4-(3-methoxylpropoxy)-3-methylpyridin-2-yl]methylsulfinyl]-6,7-dihydro-1H-[1,4]dioxino[2,3-f]benzo[d]imidazole |
| 7 | | 2-[[4-(3-methoxylpropoxy)-3-methylpyridin-2-yl]methylsulfinyl]-1H,5H-imidazo[5,4-f]benzo[d]imidazole |
| 8 | | 2-[(3,5-dimethyl-4-methoxylpyridin-2-yl)methylsulfinyl]-1H,5H-imidazo[5,4-f]benzo[d]imidazole |
| 9 | | 2-[[3-methyl-4-(2,2,2-trifluoroethoxyl)pyridin-2-yl]methylsulfinyl]-1H,5H-imidazo[5,4-f]benzo[d]imidazole |
| 10 | | 2-[(3,4-dimethoxylpyridin-2-yl)methylsulfinyl]-1H,5H-imidazo[5,4-f]benzo[d]imidazole |

TABLE 1-continued

Part of compounds of the present invention

| No. | Structural formula | Chemical name |
|---|---|---|
| 11 | 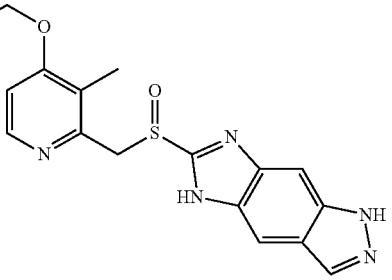 | 6-[[4-(3-methoxylpropoxy)-3-methylpyridin-2-yl]methylsulfinyl]-1,5-dihydro-imidazo[4,5-f]indazole |
| 29 | 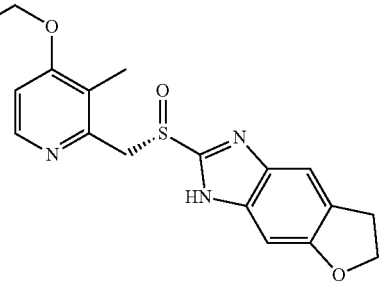 | (S)-2-[[[4-(3-methoxylpropoxy)-3-methyl-2-pyridyl]methyl]sulfinyl]-6,7-dihydro-3H-benzofuro[5,6-d]imidazole |
| 30 | 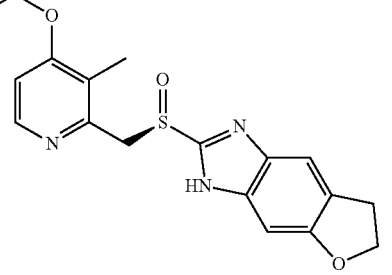 | (R)-2-[[[4-(3-methoxylpropoxy)-3-methyl-2-pyridyl]methyl]sulfinyl]-6,7-dihydro-3H-benzofuro[5,6-d]imidazole |

In the present invention, the term "$C_{1-6}$ alkyl" represents a straight, branched or cyclic alkyl having 1-6 carbon atoms, such as methyl, ethyl, n-propyl, iso-propyl, n-butyl, iso-butyl, sec-butyl, tert-butyl, n-pentyl, iso-pentyl, 2-methylbutyl, neo-pentyl, 1-ethylpropyl, n-hexyl, iso-hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1-methyl-2-methylpropyl, cyclopropyl, cyclobutyl, 1-methylcyclobutyl, cyclopentyl, cyclohexyl, etc. Correspondingly, in the present invention, the term "$C_{1-4}$ alkyl" represents a straight, branched or cyclic alkyl having 1-4 carbon atoms, such as is methyl, ethyl, n-propyl, iso-propyl, n-butyl, iso-butyl, sec-butyl and tert-butyl.

In the present invention, the term "$C_{1-6}$ alkoxyl" represents a monovalent group having formula ($C_{1-6}$ alkyl)-O—, in which alkyl has the above definition. Representative $C_{1-6}$ alkoxyl groups include, for example, methoxyl, ethoxyl, n-propoxy, iso-propoxy, n-butoxy, sec-butoxy, iso-butoxy, tert-butoxy, n-pentoxy, neo-pentoxy, n-hexoxy, etc. Correspondingly, in the present invention, the term "$C_{1-4}$ alkoxyl" represents an alkoxyl having 1-4 carbon atoms, such as methoxyl, ethoxyl, n-propoxy, iso-propoxy, n-butoxy, sec-butoxy, iso-butoxy, tert-butoxy, etc.

In the present invention, the term "halogen atom" represents fluorine atom, chlorine atom, bromine atom and/or iodine atom.

In the present invention, "halo-" in the term "halo$C_{1-6}$ alkyl and halo$C_{1-6}$ alkoxyl" represents one or more hydrogen atoms on the carbon atoms of $C_{1-6}$ alkyl and $C_{1-6}$ alkoxyl are substituted with halogen atoms.

In the present invention, the examples of the term "5- to 7-membered monocycle having 1-3 oxygen atoms, sulfur atoms and/or nitrogen atoms" comprise pyrrole, dihydropyrrole, pyrrolidine, imidazole, 4,5-dihydroimidazole, imidazolidine, pyrazole, 4,5-dihydropyrazole, pyrazolidine, 1,2,3-triazole, 1,2,4-triazole, furan, tetrahydrofuran, pyridine, piperidine, pyridazine, pyrimidine, pyrazine, piperazine, 1,2,3-triazine, 1,2,4-triazine, 1,3,5-triazine, 2H-pyran, 3,4-dihydro-2H-pyran, 4H-pyran, tetrahydropyran, 1,4-dioxacyclohexadiene, 1,4-dioxacyclohexane, 1,3-dioxacyclohexane, 2H-1,2-oxazine, 4H-1,2-oxazine, 6H-1,2-oxazine, 2H-1,3-oxazine, 4H-1,3-oxazine, 5,6-dihydro-4H-1,3-oxazine, 6H-1,3-oxazine, 2H-1,4-oxazine, 4H-1,4-oxazine, morpholine, oxacycloheptane, oxacycloheptatriene, azacycloheptatriene, 1,4-diazacycloheptatriene, etc.

In the present invention, the examples of the term "5- to 7-membered monocycle having 1-2 oxygen atoms, sulfur atoms and/or nitrogen atoms" represents the examples of "5- to 7-membered monocycle having 1-3 oxygen atoms, sulfur atoms and/or nitrogen atoms" which have 1-2 oxygen atoms, sulfur atoms and/or nitrogen atoms.

In the present invention, the term "effective amount" represents an amount of the compound of the present invention that can achieve the prophylaxis and/or treatment of disease when a subject in such need is administered with the compound.

In another aspect, the present invention provides a method for preparing the compound of Formula (I), comprising but not being limited to the following method.

The method for preparing the compound of the present invention comprises: performing a substitution reaction of a compound of Formula (II) and a compound of Formula (III) to form a compound of Formula (I'), and converting the Formula (I') in the presence of m-chloro-peroxybenzoic acid to obtain a compound of Formula (I),

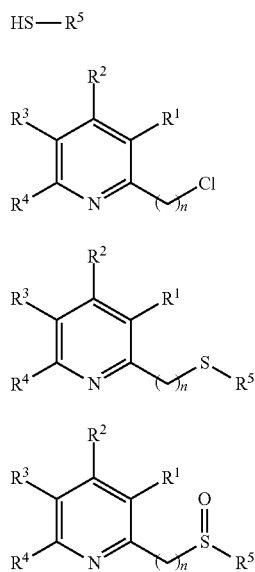

in which, $R^1$, $R^2$, $R^3$, $R^4$, $R^5$ and n have the above definitions.

The reaction equation is as follows:

(1) when $R^5$ represents

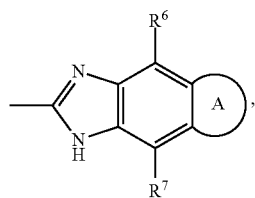

the reaction equation is as follows:

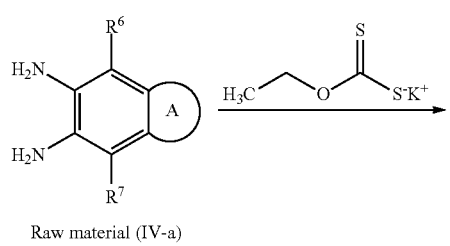

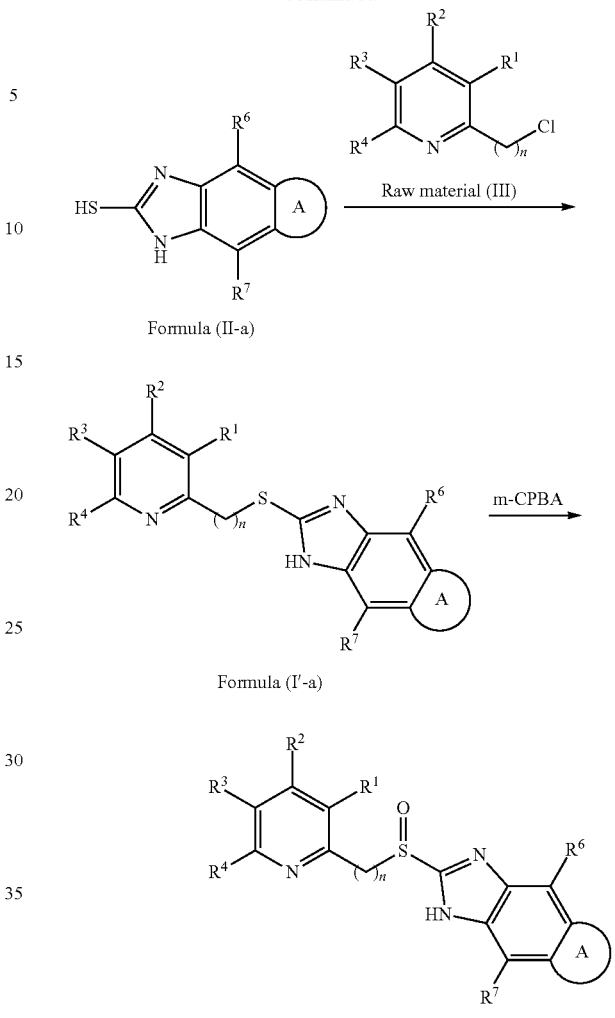

Reaction Steps:

Step 1: Preparation of a Compound of Formula (II-a)

Raw material (IV-a) is dissolved in anhydrous ethanol, potassium ethylxanthogenate is added, stirred, remove solvent, water and concentrated hydrochloric acid are added, extracts with ethyl acetate, combine organic layers, then washed with water and saline, dried, concentrated under vacuum to obtain the compound of Formula (II-a).

Step 2: Preparation of a Compound of Formula (I'-a)

The compound of Formula (II-a) and NaOH are dissolved in acetone and water, stirred, a raw material (III) is added, stirred at room temperature, filtered, the filter cake is washed with acetone and water, dried to obtain the compound of Formula (I'-a).

Step 3: Preparation of a Compound of Formula (I-a)

The compound of Formula (I'-a) is dissolved in dichloromethane, stirred, m-chloro-peroxybenzoic acid (m-CPBA) is added, stirred during reaction, the reaction mixture is added to saturated sodium bicarbonate, extracting with dichloromethane, organic layers are combined, then washed with saline, dried, concentrated under vacuum, purified by column chromatography to obtain the compound of Formula (I-a).

(2) When $R^5$ represents

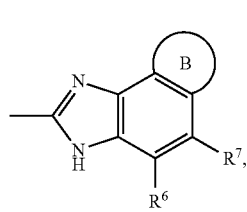

the reaction equation is as follows:

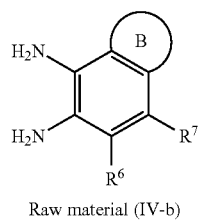 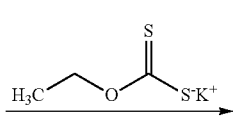

Raw material (IV-b)

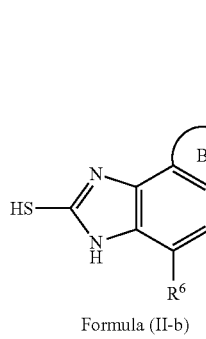 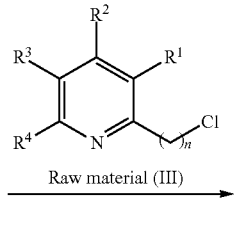

Formula (II-b)

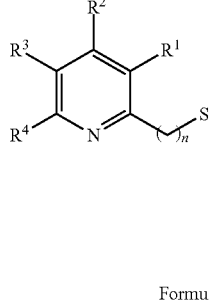

Formula (I'-b)

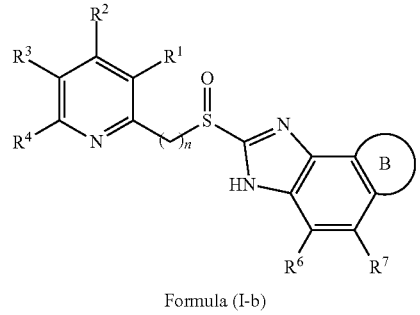

Formula (I-b)

Reaction steps: identical to the reaction steps for preparing the compound of Formula (I-a).

(3) when $R^5$ represents

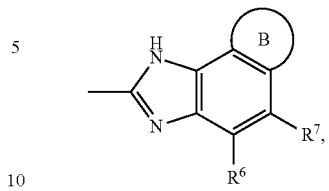

the reaction equation is as follows:

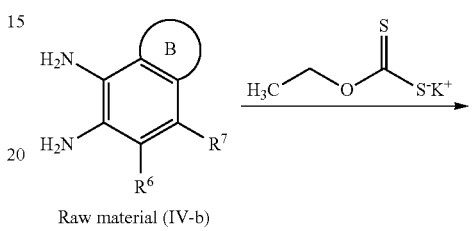

Raw material (IV-b)

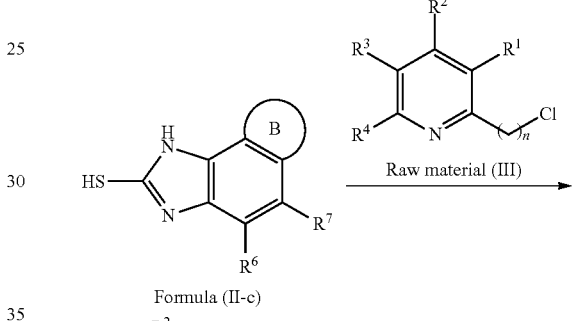

Formula (II-c)

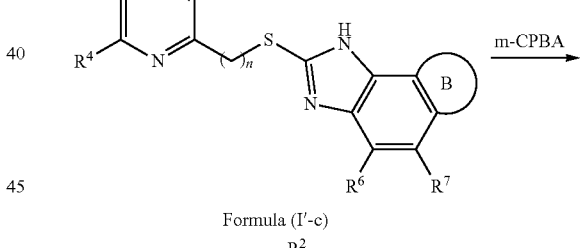

Formula (I'-c)

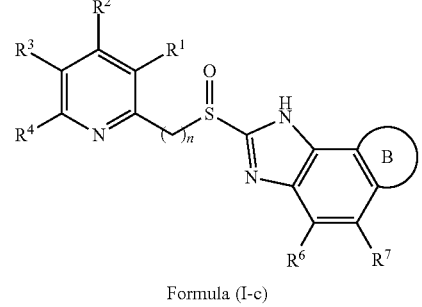

Formula (I-c)

Reaction steps: identical to the reaction steps for preparing the compound of Formula (I-a).

Ring A, ring B, $R^1$, $R^2$, $R^3$, $R^4$, $R^6$, $R^7$ and n have the above definitions.

The raw materials (IV-a), (IV-b) and (IV-c) in the above reaction equations can be commercially obtained or synthesized via simple methods as well-known by those skilled in the art.

In a further aspect, the present invention provides a compound of Formula (I'), or a stereoisomer, solvate or pharmaceutically acceptable salt thereof:

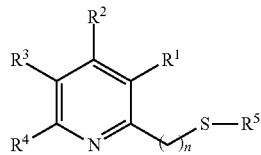

(I')

in which, $R^1$, $R^2$, $R^3$, $R^4$, $R^5$ and n have the above definitions.

In a further aspect, the present invention provides a compound of Formula (II), or a stereoisomer, solvate or pharmaceutically acceptable salt thereof:

(II), in which, $R^5$ has the above definitions.
wherein,

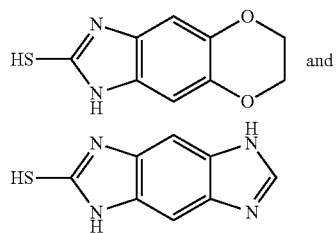

are excluded.

The compound of the present invention can be present in form of tautomers, which have different hydrogen linking points due to the migration of one or more double bonds. All these tautomers and mixtures thereof are in the scope of the present invention. For example, as for the compound of Formula (I), (I') or (II) of the present invention and the intermediates used in the process for preparing them, when $R^5$ represents

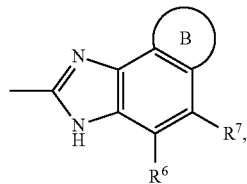

imidazole ring may convert into its tautomer

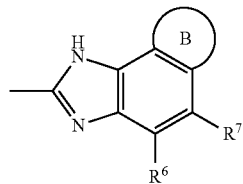

due to the dissociation of electrons on the imidazole ring. Hence, when one of them is prepared, its tautomer is correspondingly prepared at the same time. For example, when Formula (II-b) is prepared, Formula (II-c) is correspondingly prepared at the same time; when Formula (I'-b) is prepared, Formula (I'-c) is correspondingly prepared at the same time; and when Formula (I-b) is prepared, Formula (I-c) is correspondingly prepared at the same time. All the compounds of the present invention involving the above situations and intermediates for preparing them are equate and in the scope of the present invention.

All stereoisomers of the compound of the present invention are comprised in the present invention. The compound of the present invention has chiral atoms or asymmetric centers, and thus the correspondingly generated enantiomers are comprised in the present invention. The compound of the present invention has cyclic structures, and thus the correspondingly generated cis-trans-isomers are also comprised in the present invention. The conformational isomers caused by ration or distortion of carbon-carbon single bond are also comprised in the present invention.

In a further aspect, the present invention provides a method for preparing the enantiomers of the compound of Formula (I), the method comprising: the compound of Formula (I') is added to a chiral resolution agent to obtain the desired compound.

The chiral resolution reagent comprises, for example, D-(−)-diethyl tartrate, L-(+)-diethyl tartrate, D-(−)-dimethyl tartrate, L-(+)-dimethyl tartrate, D-(+)-di-p-toluoyltartaric acid, L-(−)-di-p-toluoyltartaric acid, D-(+)-bibenzoyltartaric acid, L-(−)-bibenzoyltartaric acid, (1S,2S)-(−)-1,2-diphenylethylenediamine, (1R,2R)-(+)-1,2-diphenylethylenediamine, D-(−)-diisopropyl tartrate, L-(+)-diisopropyl tartrate, D-(+)-di-p-toluoyltartaric acid, L-(−)-di-p-toluoyltartaric acid, D-(+)-bibenzoyltartaric acid, L-(−)-bibenzoyltartaric acid, D(+)-malic acid, (1S,2R)-(+)-2-amino-1,2-diphenylethanol, (1R,2S)-(−)-2-amino-1,2-diphenylethanol, 2,4-dichloro-α-phenylethylamine, D-di-p-anisoyltartaric acid, L-di-p-anisoyltartaric acid, R-(−)-o-chloro-mandelic acid, S-(+)-o-mandelic acid, R-bisphenol, S-bisphenol, S-mandelic acid, R-mandelic acid, R-(+)-methylbenzylamine, S-(−)-phenylethylamine, D-Camphorsulfonic acid, D-camphor sulfonic acid, L-(−)camphor sulfonic acid, D-camphoric acid, L-camphoric acid, etc.

The compounds of the present invention, stereoisomers thereof, pharmaceutically acceptable salts thereof can be in the form of solvates. When the solvates are hydrates, the hydration can be performed during the preparation process or performed gradually by utilizing the hygroscopicity of original anhydrous products.

The pharmaceutically acceptable salts of the compounds of the present invention are not specifically limited, including inorganic acid addition salts, organic acid addition salts, amino acid salts and metal salts.

As for the salts of the compound of Formula (I), the preferred salts are the salts formed by addition with pharmaceutically acceptable alkalis, such as lithium salts, sodium salts, potassium salts, calcium salts, magnesium salts, and bismuth salts.

As for the salts of the compound of Formula (I'), the preferred salts are the salts formed by addition with pharmaceutically acceptable acids, such as hydrochlorides, sulfates, nitrates, phosphates, hydrobromides, hydroiodides, formates, acetates, propionates, oxalates, malonates, succinates, maleates, fumarates, lactates, malates, citrates, tartrates, mesylates, ethylene sulfonate, benzene sulfonate, toluene-sulfonates, tetrafluoroborates, arginine salts, aspartates and glutamates;

The compound of the present invention can specifically inhibit $H^+$, $K^+$-ATP enzymes of secretion of microtubules constituting parietal cell top membrane and of tubular bubbles in cytoplasm, induce irreversible inhibition of these enzymes, thereby effectively inhibiting gastric secretion, and thus can be used for prophylaxis and/or treatment of peptic ulcer and diseases associated with gastric acid, such as gastritis, gastric ulcer, duodenal ulcer, reflux esophagitis, zollinger-ellison syndrome, etc.

The compound of the present invention can elevate the pH value in stomach, facilitate hemostasis induced by platelet agglutination and plasma coagulation function, avoiding the quick digestion of sludged blood in gastric acid having pH<5.0, and thus can be used for prophylaxis and/or treatment of peptic ulcer hemorrhage, acute gastric mucosa injury caused by non-steroidal anti-inflammatory drugs, and ulcer hemorrhage under stress state, for prevention of gastric acid backflow combined aspiration pneumonitis in patients of general anesthesia or major operation as well as weak and coma patients.

In a further aspect, the present invention provides a use of the compound of Formula (I) or stereoisomers, solvates or pharmaceutically acceptable salts thereof in the prophylaxis and/or treatment of peptic ulcer, ulcer hemorrhage and diseases associated with gastric acid in a subject.

In a further aspect, the present invention provides a method for prophylaxis and/or treatment of peptic ulcer, ulcer hemorrhage and diseases associated with gastric acid in a subject, the method comprising: administering the subject with the compound of Formula (I) or stereoisomers, solvates or pharmaceutically acceptable salts thereof in a prophylactically and/or therapeutically effective amount.

In a further aspect, the present invention provides a use of the compound of Formula (I) or stereoisomers, solvates or pharmaceutically acceptable salts thereof in the manufacture of a medicament, the medicament being used for prophylaxis and/or treatment of peptic ulcer, ulcer hemorrhage and diseases associated with gastric acid in a subject.

In a further aspect, the present invention provides a pharmaceutical composition, comprising a compound of the present invention, or a stereoisomer, solvate or pharmaceutically acceptable salt thereof, and one or more pharmaceutically acceptable excipients.

In one embodiment of this aspect, the pharmaceutical composition of the present invention comprises in addition to a compound of the present invention, or a stereoisomer, solvate or pharmaceutically acceptable salt thereof, further other active ingredients useful in prophylaxis and/or treatment of peptic ulcer, ulcer hemorrhage and diseases associated with gastric acid. The other active components used in the pharmaceutical composition of the present invention can be:

1. Antibacterial agents, such as β-lactam antibiotics, such as Amoxicillin, Ampicillin, Cefalotin, Cefaclor or Cefixime; macrolides, such as Erythromycin or Clarithromycin; tetracyclines, such as Tetracycline or Doxycycline; 4) aminoglycosides, such as Gentamycin, Kanamycin or Amikacin; quinolones, such as Norfloxacin, Ciprofloxacin or Enoxacin; others, such as Metronidazole, Nitrofurantoin or Chloromycetin; or, pharmaceutical formulations containing a bismuth salt, such as formulations of acid form bismuth citrate, bismuth subsalicylate, bismuth subcarbonate, bismuth subnitrate, bismuth subgallate.

2. Antacid agents, such as aluminum hydroxide, magnesium hydroxide, magnesium carbonate and magnesium aluminate, etc.;

3. Tranquilizers, such as tranquilizing agents, including diazacycloheptatriene, etc.;

4. Spasmolytics, such as Bietamiverine and Camylofin, etc.;

5. Anticholinergic agents, such as oxyphenylepimine and phenol urea, etc.;

6. Local anaesthetics, such as Tetracaine and Procaine, etc.;

7. Non-steroidal anti-inflammatory agents, such as Indometacin, Aspirin and Naproxen, etc.;

8. Steroids and nitrite counteractants, such as ascorbic acid and aminosulfonic acid, etc.;

9. Other agents for treatment of gastric ulcer, such as pirenzipine, etc.;

10. Prostaglandin drugs, such as 16,16-dimethylPGE2, etc.;

11. Histamine $H_2$-antagonists, such as cimetidine, etc.

In the pharmaceutical composition of the present invention, the used "pharmaceutically acceptable excipients" can be any common excipients in the field of medicine preparations. The selection of specific excipients will depend on the administration manner for treatment of specific patients or type and state of disease. The method for preparing a suitable pharmaceutical composition for a specific administration manner is well known by those skilled in the medicine field. For example, the pharmaceutically acceptable excipients can comprise common pharmaceutically acceptable diluents, carriers, fillers, binders, wetting agents, disintegrants, absorption enhancers, surfactants, adsorption carriers and lubricants, etc. If necessary, flavoring agents, preservatives and sweeting agents etc. can be added to the pharmaceutical composition.

The pharmaceutical composition of the present invention can be administered via any manner known in the art, for example, via oral, spray inhalation, rectum, nasal cavity, vaginal administration or topical administration, or via parenteral administration, such as via subcutaneous, intravenous, intramuscularly, intraperitoneally, intrathecal, intraventricular, intrasternal or intracranial injection, or infusion, among which, preferably administered via oral, intramuscularly, intraperitoneally or intravenous injection.

When it is used for oral administration, it can be processed to form a conventional solid preparation, such as tablet, capsule, pill, granule, etc.; or to form an oral liquid preparation, such as oral solution, oral suspension, syrups, etc. When it is an oral preparation, suitable fillers, binders, disintegrants, lubricants etc. can be added.

When it is used for injection administration, it can be processed to form a conventional injection, injection aseptic powder and injection concentrated liquid. When it is an injection preparation, it can be prepared by a conventional method in the pharmaceutical field; when an injection is prepared, additives may not be added, or suitable additives may be added according to the properties of drug.

No matter being used for human medical treatment or veterinary medicine, the compound of the present invention has a daily dose of 1-3000 mg, preferably 5-2000 mg, more preferably 5-1500 mg, of the compound of Formula (I) for oral administration; a daily dose of 1-1500 mg, preferably 5-1000 mg, of the compound of Formula (I) for injection administration. If necessary, the compound or pharmaceutical composition of the present invention can be administered in multiple doses to achieve the desired effects. However, those skilled in the art know that, if necessary, the administration can be performed beyond the above dose ranges, according to the kinds and body weight of subjects, the properties and severity of diseases, the types and administration manners of the preparations, and the cycle and interval of administration.

In comparison with the prior art, the compound of the present invention is not influenced by $CYP_2C_{19}$ enzyme metabolism, thereby reducing administration difference in population; can significantly inhibit gastric acid secretion in mammals, has no potential toxic and side effects, no gastrointestinal tract irritation; has less drug interaction, is safe and effective, can be used for manufacture of a medicament for treatment and/or prophylaxis of digestive tract ulcer, and the medicament has quick onset, strong potency, long half-life, and stable acid inhibition effects.

EXEMPLARY MODES FOR CARRYING OUT THE INVENTION

The following experimental examples and preparation examples further illustrate the beneficial effects and preparation of the compound of the present invention, but the present invention is not intended to be limited to these experimental examples and preparation examples.

Example 1

Preparation of 2-[[4-(3-methoxylpropoxy)-3-methylpyridin-2-yl]methylsulfinyl]-6,7-dihydro-3H-benzofuro[5,6-d]midazole (Compound 1)

Step 1: Preparation of 5-nitro-2,3-dihydrobenzofuran

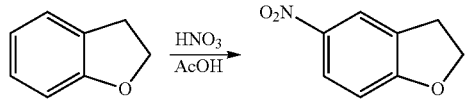

2,3-dihydrobenzofuran (5 g, 41.6 mmol) was dissolved in 35 mL of acetic acid, and ¼ $HNO_3$ (0.9 mL, 45.4 mmol) was added dropwise. At the beginning of reaction, it was heated to 70° C., then the residual $HNO_3$ was added. After 0.5 hour, the reaction was cooled, added into ice-water, and then neutralized with $Na_2CO_3$. The water layer was extracted with ethyl acetate. The organic layers were combined and dried, concentrated under vacuum, purified by column chromatography to obtain a product (1 g, 14.6%).

Step 2: Preparation of 5-amino-2,3-dihydrobenzofuran

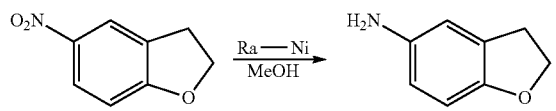

The product (1 g, 6.1 mmol) obtained in Step 1, Raney Ni (0.1 g) and MeOH (10 mL) were used for hydrogenation at room temperature and hydrogen pressure of 50 PSI, until the reaction was finished. The catalyst was removed by filtration, the fitrate was concentrated under vacuum to obtain a product (800 mg, 97.2%).

Step 3: Preparation of 5-acetylamino-2,3-dihydrobenzofuran

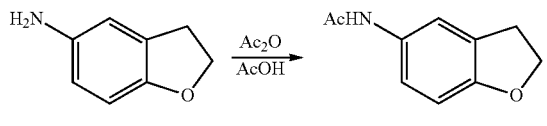 [SMILES: "Ac2O" ; "AcOH" ; Nc1ccc2c(c1)CCO2 ; CC(=O)Nc1ccc2c(c1)CCO2]

The product (5.2 g, 38.5 mmol) obtained in Step 2 was dissolved in AcOH (20 mL) and $Ac_2O$ (5 mL), heated to 60° C., reacted for 12 h, and concentrated to obtain a crude product (6 g, 88.0%).

Step 4: Preparation of 5-acetylamino-6-nitro-2,3-dihydrobenzofuran

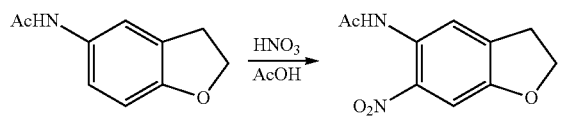

The product obtained in Step 3 (6.0 g, 33.9 mmol) was dissolved in AcOH (100 mL), then $HNO_3$ (1.9 mL, 47.5 mmol) was added. The reaction mixture was stirred at room temperature for 1 h, then poured into ice-water. The water layer was extracted with ethyl acetate. The organic layer was dried, concentrated, purified by column chromatography to obtain a product (7.0 g, 93.3%).

Step 5: Preparation of 5-amino-6-nitro-2,3-dihydrobenzofuran

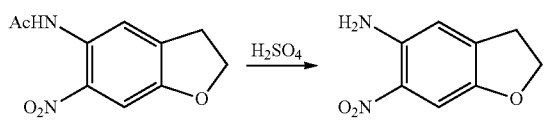

The product obtained in Step 4 (7.0 g, 31.5 mmol) and 2 mol/L $H_2SO_4$ solution (200 mL) were heated to reflux for 6 h. Then the reaction mixture was cooled to 0° C., filtered, washed with water, concentrated under vacuum and dried to obtain a product (4.0 g, 70%).

Step 6: Preparation of 5,6-diamino-2,3-dihydrobenzofuran

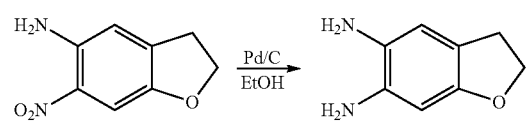

The product obtained in Step 5 (2.5 g, 13.9 mmol) and Pd/C (0.5 g) were dissolved in EtOH (50 mL), hydrogenated in a Parr hydrogenation apparatus at room temperature and a hydrogen pressure of 50 PSI for 12 h. The catalyst was removed by filtration, the ethanol solution of the product was directly used in the next step of reaction.

Step 7: Preparation of 6-mercapto-7H-2,3-dihydrobenzofuro[5,6-d]imidazole

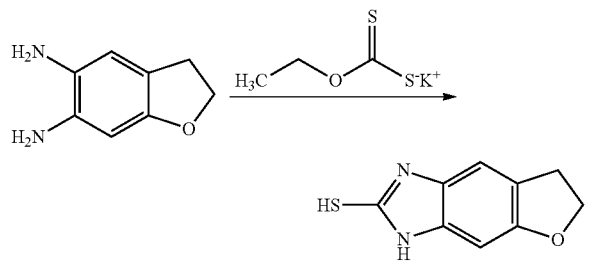

The product obtained in Step 6 (2.1 g, 13.9 mmol) was dissolved in anhydrous ethanol (50 mL). Potassium ethylxanthogenate (3.3 g, 20.8 mmol) was added, stirred for 5 h. The solvent was removed, water and concentrated hydrochloric acid were added, and the reaction mixture was adjusted to pH 3, extracted with ethyl acetate. The organic layers were combined and washed with water and saline, dried, concentrated under vacuum to obtain a product (1.5 g, 56%)

Step 8: Preparation of 2-[[4-(3-methoxylpropoxy)-3-methylpyridin-2-yl]methylsulfo]-6,7-dihydro-3H-benzofuro[5,6-d]imidazole

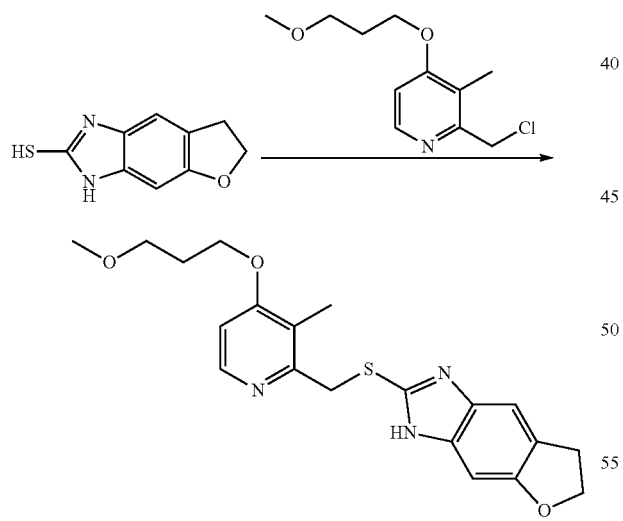

The product obtained in Step 7 (1.5 g, 7.8 mmol) and NaOH (0.78 g, 19.5 mmol) were dissolved in acetone (10 mL) and water (10 mL), stirred, added with 2-(chloromethyl)-4-(3-methoxylpropoxy)-3-methylpyridine (1.79 g, 7.8 mmol), stirred at room temperature for 2 h, filtered. The filter cake was washed with acetone and water (v:v=1:1), dried to obtain a product (1.6 g, 53.3%).

Step 9: Preparation of Compound 1

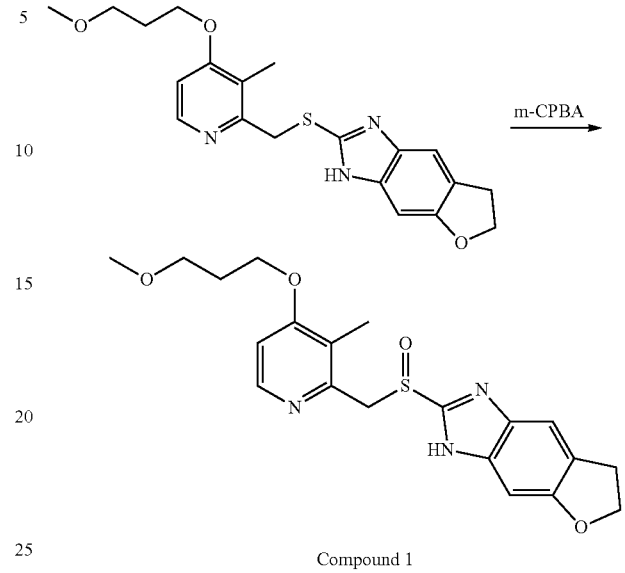

The product obtained in Step 8 (1.6 g, 4.16 mmol) was dissolved in dichloromethane (20 mL), stirred at −78° C., m-chloroperbenzoic acid m-CPBA (0.72 g, 4.16 mmol) was added in 3 batches within 1 h, stirred for 30 min. The reaction mixture was added to saturated $NaHCO_3$, extracted with dichloromethane, the organic layers were combined and then washed with saline, dried, vacuum concentrated, purified by column chromatography to obtain a product (1.6 g, 95.8%).

$^1$H-NMR ($CDCl_3$, 600 MHz) δ: 2.03 (2H, m), 2.14 (3H, s), 3.32 (3H, s), 3.25 (2H, t), 3.57 (2H, t), 4.08 (2H, t), 4.61 (2H, t), 4.72 (1H, d), 4.77 (1H, d), 6.73 (2H, m), 7.42 (1H, d), 8.30 (1H, d), 12.22 (1H, s).

Step 10: Preparation of sodium salt of Compound 1

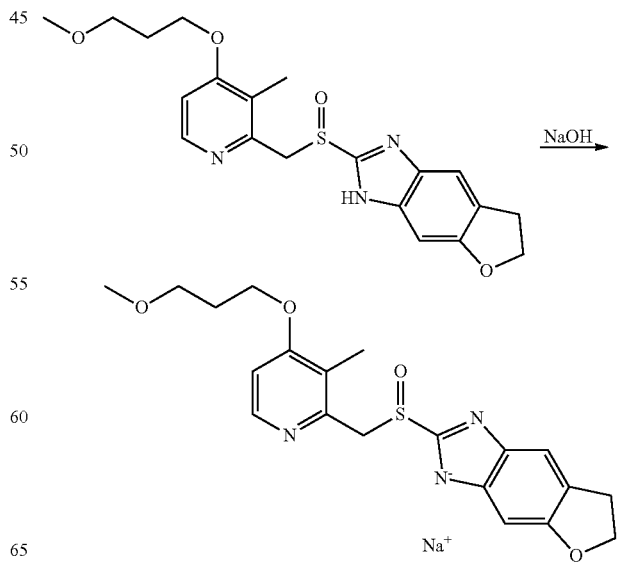

The product obtained in Step 9 (1.6 g, 4.0 mmol) was added to 0.1 mol/L NaOH solution (20 mL), stirred at room temperature for 1 h, diluted with dichloromethane, washed with saturated saline, dried, concentrated under vacuum to obtain a product (1.08 g, 63.5%).

Molecular formula: $C_{20}H_{22}N_3NaO_4S$; molecular weight: 423.46; MS: 402 (M+H$^+$)

$^1$H-NMR (400 MHz, DMSO-d$_6$) δ: 1.95 (2H, m), 2.11 (3H, s), 3.25 (3H, s), 3.27 (2H, t), 3.46 (2H, t), 4.08 (2H, t), 4.55 (2H, t), 4.63 (1H, d), 4.75 (1H, d), 6.87 (1H, s), 6.91 (1H, d), 7.45 (1H, t), 8.20 (1H, d).

Example 2

Preparation of 2-[(4-methoxyl-3,5-dimethylpyridin-2-yl)methylsulfinyl]-6,7-dihydro-3H-benzofuro[5,6-d]imidazole (Compound 2)

Step 1 to Step 7 were performed by referring to the Step 1 to Step 7 of Example 1.

Step 8: Preparation of 2-[(4-methoxyl-3,5-dimethylpyridin-2-yl)methylsulfo-6,7-dihydro-3H-benzofuro[5,6-d]imidazole

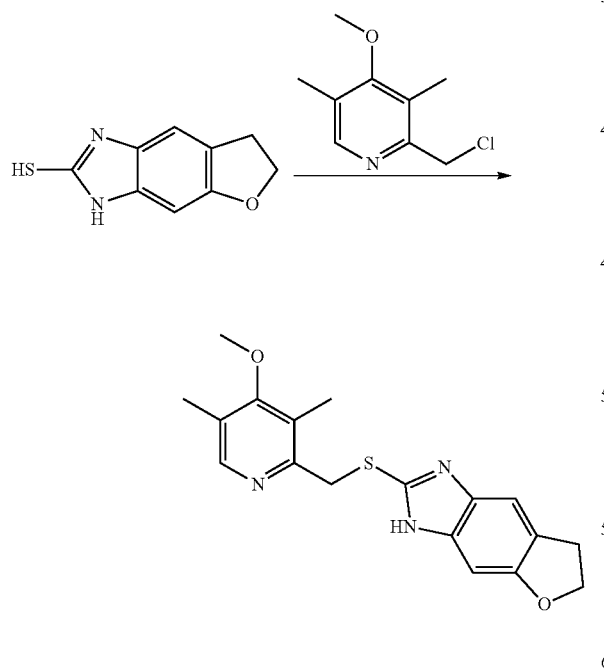

By referring to the Step 8 of Example 1, 6-mercapto-7H-2,3-dihydrobenzofuro[5,6-d]imidazole (1.5 g, 7.8 mmol), NaOH (0.78 g, 19.5 mmol), acetone (10 mL), water (10 mL) and 2-(chloromethyl)-4-methoxyl-3,5-dimethylpyridine (1.45 g, 7.8 mmol) were used to obtain a product (1.51 g, 56.7%).

Step 9: Preparation of Compound 2

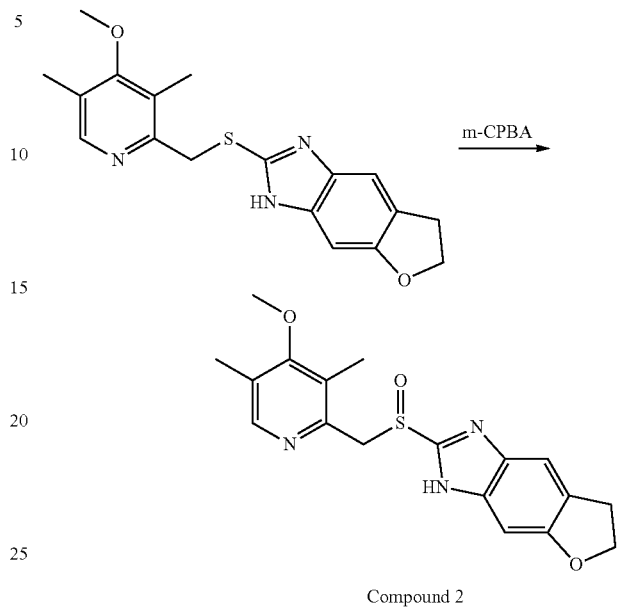

Compound 2

By referring to the Step 9 of Example 1, 2-[(4-methoxyl-3,5-dimethylpyridin-2-yl)methylsulfo]-6,7-dihydro-3H-benzofuro[5,6-d]imidazole (1.42 g, 4.16 mmol), dichloromethane (20 mL), m-CPBA (0.72 g, 4.16 mmol), were used to obtain a product (1.38 g, 92.9%).

$^1$H-NMR (DMSO, 600 MHz) δ: 2.21 (6H, s), 3.18 (2H, t), 3.69 (3H, s), 4.34 (1H, d), 4.43 (2H, t), 4.70 (1H, d), 6.75 (1H, s), 7.27 (1H, s), 8.22 (1H, s), 12.20 (1H, b).

Step 10: Preparation of sodium salt of Compound 2

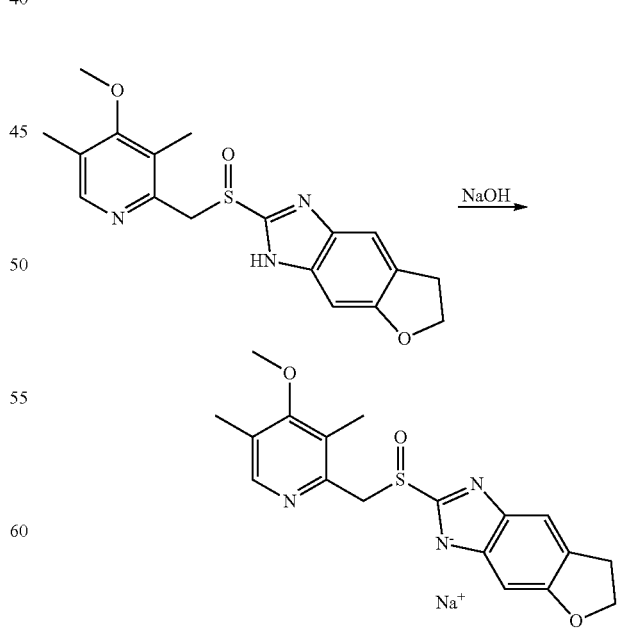

By referring to Step 10 of Example 1, 2-[(4-methoxyl-3,5-dimethylpyridin-2-yl)methylsulfinyl]-6,7-dihydro-3H-benzofuro[5,6-d]imidazole (1.43 g, 4.0 mmol), 0.1 mol/L NaOH solution (20 mL), were used to obtain a product (1.0 g, 66.4%).

Molecular formula: $C_{18}H_{18}N_3NaO_3S$; molecular weight: 379.41; MS: 358 (M+H$^+$)

Example 3

Preparation of 2-[[3-methyl-4-(2,2,2-trifluoroethoxyl)pyridin-2-yl]methylsulfinyl]-6,7-dihydro-3H-benzofuro[5,6-d]imidazole (Compound 3)

Step 1 to Step 7 were performed by referring to the Step 1 to Step 7 of Example 1.

Step 8: Preparation of 2-[[3-methyl-4-(2,2,2-trifluoroethoxyl)pyridin-2-yl]methylsulfo]-6,7-dihydro-3H-benzofuro[5,6-d]imidazole

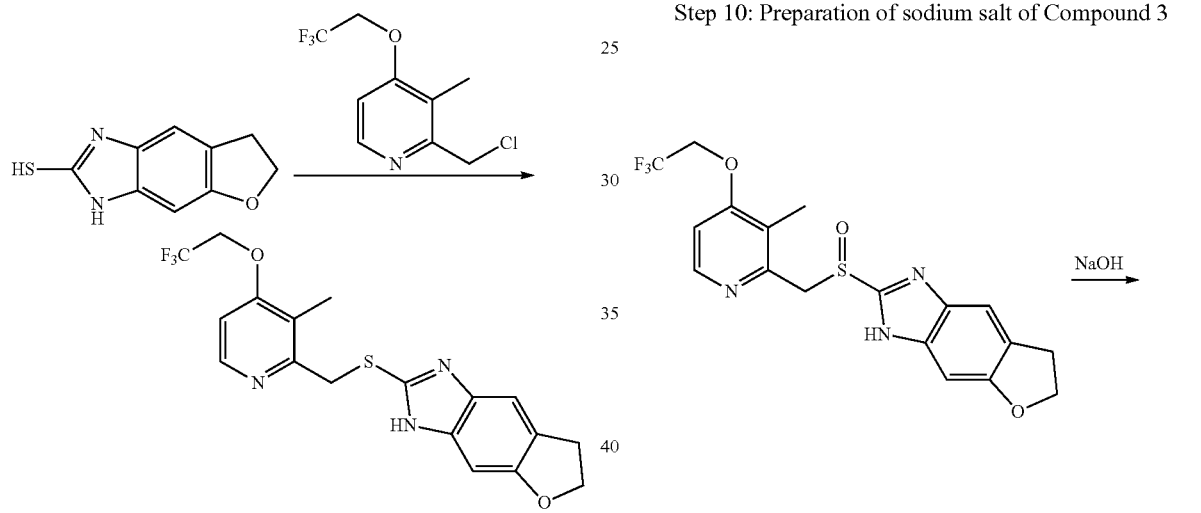

By referring to the Step 8 of Example 1, 6-mercapto-7H-2,3-dihydrobenzofuro[5,6-d]imidazole (1.5 g, 7.8 mmol), NaOH (0.78 g, 19.5 mmol), acetone (10 mL), water (10 mL), 2-(chloromethyl)-3-methyl-4-(2,2,2-trifluoroethoxyl)pyridine (1.87 g, 7.8 mmol), were is used to obtain a product (1.63 g, 52.8%).

Step 9: Preparation of Compound 3

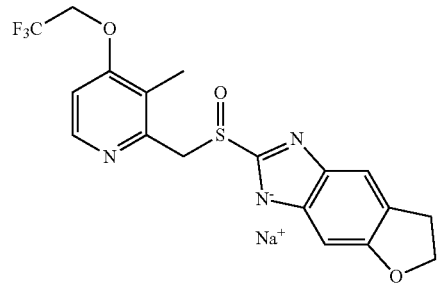

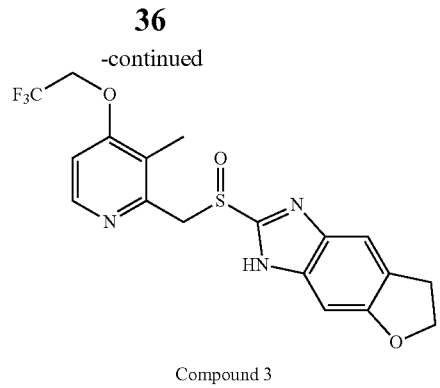

Compound 3

By referring to the Step 9 of Example 1, 2-[[3-methyl-4-(2,2,2-trifluoroethoxyl)pyridin-2-yl]methylsulfo]-6,7-dihydro-3H-benzo furo[5,6-d]imidazole (1.64 g, 4.16 mmol), dichloromethane (20 mL), m-CPBA (0.72 g, 4.16 mmol), were used to obtain a product (1.55 g, 90.7%).

Step 10: Preparation of sodium salt of Compound 3

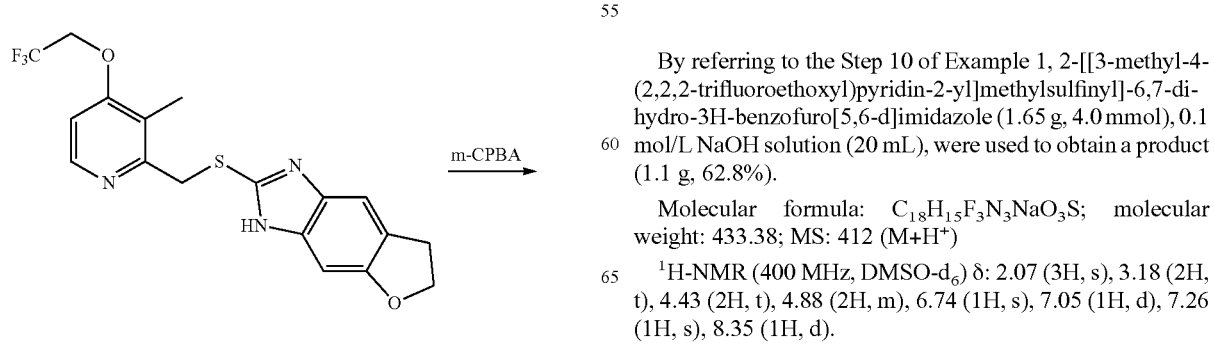

By referring to the Step 10 of Example 1, 2-[[3-methyl-4-(2,2,2-trifluoroethoxyl)pyridin-2-yl]methylsulfinyl]-6,7-dihydro-3H-benzofuro[5,6-d]imidazole (1.65 g, 4.0 mmol), 0.1 mol/L NaOH solution (20 mL), were used to obtain a product (1.1 g, 62.8%).

Molecular formula: $C_{18}H_{15}F_3N_3NaO_3S$; molecular weight: 433.38; MS: 412 (M+H$^+$)

$^1$H-NMR (400 MHz, DMSO-d$_6$) δ: 2.07 (3H, s), 3.18 (2H, t), 4.43 (2H, t), 4.88 (2H, m), 6.74 (1H, s), 7.05 (1H, d), 7.26 (1H, s), 8.35 (1H, d).

Example 4

Preparation of 2-[(3,4-dimethoxylpyridin-2-yl)methylsulfinyl]-6,7-dihydro-3H-benzofuro[5,6-d]imidazole (Compound 4)

Step 1 to Step 7 were performed by referring to the Step 1 to Step 7 of Example 1.

Step 8: Preparation of 2-[(3,4-dimethoxylpyridin-2-yl)methylsulfo]-6,7-dihydro-3H-benzofuro[5,6-d]imidazole

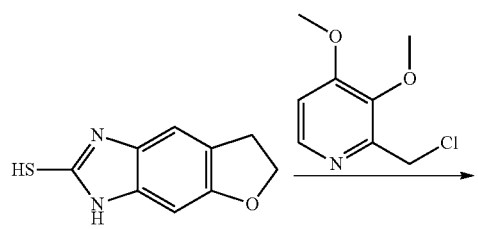

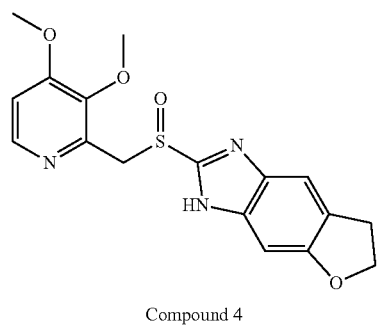

Compound 4

By referring to the Step 9 of Example 1, 2-[(3,4-dimethoxylpyridin-2-yl)methylsulfo]-6,7-dihydro-3H-benzofuro[5,6-d]imidazole (1.43 g, 4.16 mmol), dichloromethane (20 mL), m-CPBA (0.72 g, 4.16 mmol), were used to obtain a product (1.43 g, 95.4%).

$^1$H-NMR (CDCl$_3$, 600 MHz) δ: 3.32 (2H, t), 3.88 (3H, s), 3.92 (3H, s), 4.64 (3H, m), 4.85 (1H, d), 6.84 (2H, m), 7.59 (1H, s), 8.24 (1H, d), 11.60 (1H, b).

Step 10: Preparation of sodium salt of Compound 4

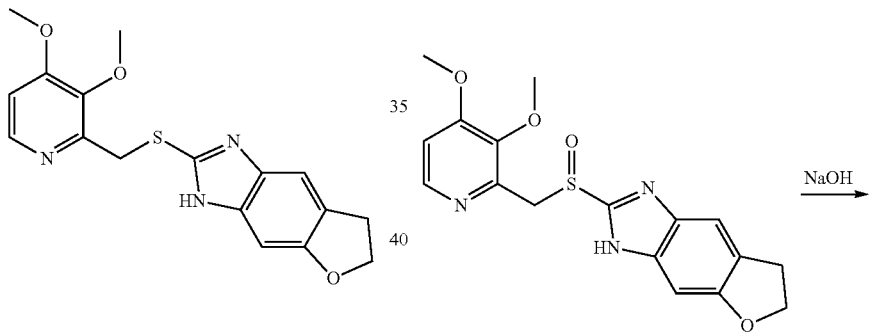

By referring to the Step 8 of Example 1, 6-mercapto-7H-2,3-dihydrobenzofuro[5,6-d]imidazole (1.5 g, 7.8 mmol), NaOH (0.78 g, 19.5 mmol), acetone (10 mL), water (10 mL), 2-chloromethyl-3,4-dimethoxylpyridine (1.46 g, 7.8 mmol), were used to obtain a product (1.61 g, 60.2%).

Step 9: Preparation of Compound 4

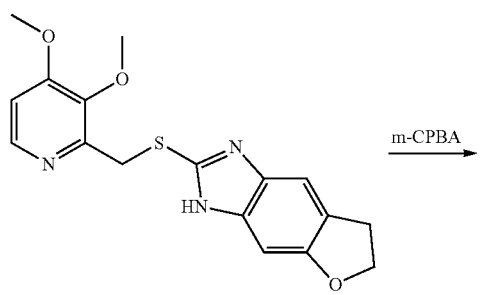

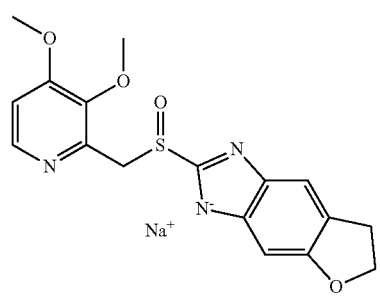

By referring to the Step 10 of Example 1, 2-[(3,4-dimethoxylpyridin-2-yl)methylsulfo]-6,7-dihydro-3H-benzofuro[5,6-d]imidazole (1.44 g, 4.0 mmol), 0.1 mol/L NaOH solution (20 mL), were used to obtain a production (0.98 g, 68.7%).

Molecular formula: $C_{17}H_{16}N_3NaO_4S$; molecular weight: 381.38; MS: 360 (M+H$^+$)

Example 5

Preparation of 2-[[4-(3-methoxylpropoxy)-3-methylpyridin-2-yl]methylsulfinyl]-3,6-dihydroimidazo[4,5-e]indazole (Compound 5)

Step 1: Preparation of 5-aminoindazole

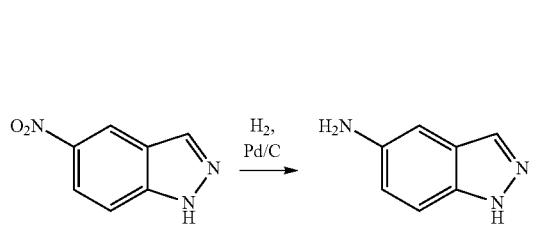 [SMILES: O=[N+]([O-])c1ccc2[nH]ncc2c1 ; Nc1ccc2[nH]ncc2c1]

By referring to the Step 6 of Example 1, 5-nitroindazole (5.0 g, 30.7 mmol), Pd/C (1.2 g), were used to obtain a product (2.6 g, 62.6%).

Step 2: Preparation of 5-acetylaminoindazole

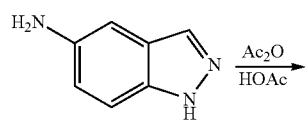

By referring to the Step 3 of Example 1, 5-aminoindazole (5 g, 37.6 mmol), AcOH (20 mL) and Ac₂O (5 mL), were used, concentrated to obtain a crude product that was directly used in the next step of reaction.

Step 3: Preparation of 4-nitro-5-acetylaminoindazole

By referring to the Step 4 of Example 1, 5-acetylaminoindazole (6 g, 34.2 mmol), HNO₃ (2.0 mL, 48 mmol), were used to obtain a product (6.9 g, 91.7%).

Step 4: Preparation of 4-nitro-5-aminoindazole

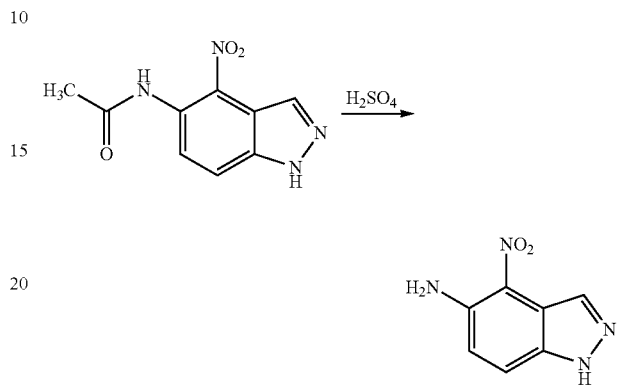

By referring to the Step 5 of Example 1, 4-nitro-5-acetylaminoindazole (6.9 g, 31.5 mmol), 2 mol/L H₂SO₄ solution (200 mL), were used to obtain a product (4.0 g, 73.6%).

Step 5: Preparation of 4,5-diaminoindazole

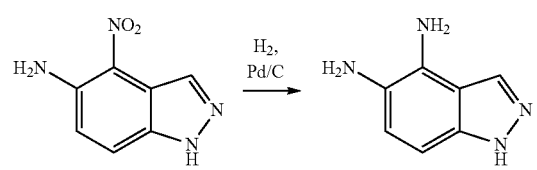 [SMILES: Nc1ccc2[nH]ncc2c1[N+](=O)[O-] ; Nc1ccc2[nH]ncc2c1N]

By referring to the Step 6 of Example 1, 4-nitro-5-aminoindazole (2.5 g, 14.0 mmol), Pd/C (0.25 g), were used to obtain a product (1.4 g, 65.5%).

Step 6: Preparation of 2-mercapto-1H,6H-imidazole[4,5-e]indazole

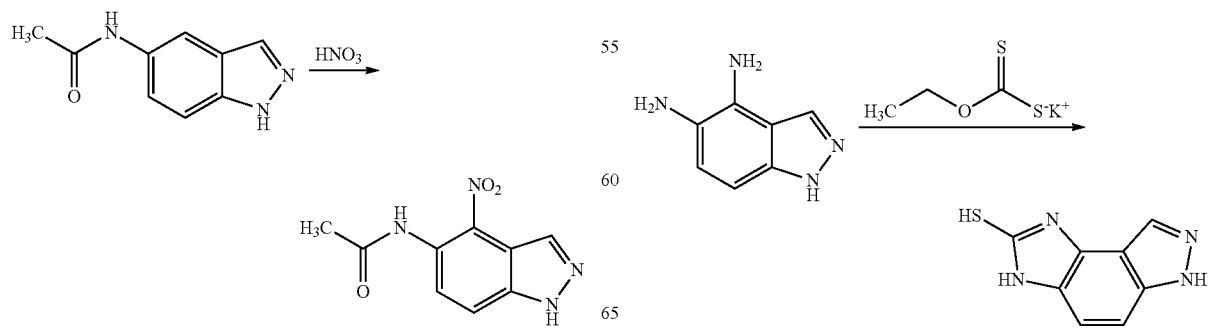

By referring to the Step 7 of Example 1, 4,5-diaminoindazole (2.0 g, 13.5 mmol), potassium ethylxanthate (3.2 g, 20.2 mmol), were used to obtain a product (1.5 g, 59.2%).

Step 7: Preparation of 2-[[4-(3-methoxylpropoxy)-3-methylpyridin-2-yl]methylsulfo]-3,6-dihydroimidazo[4,5-e]indazole

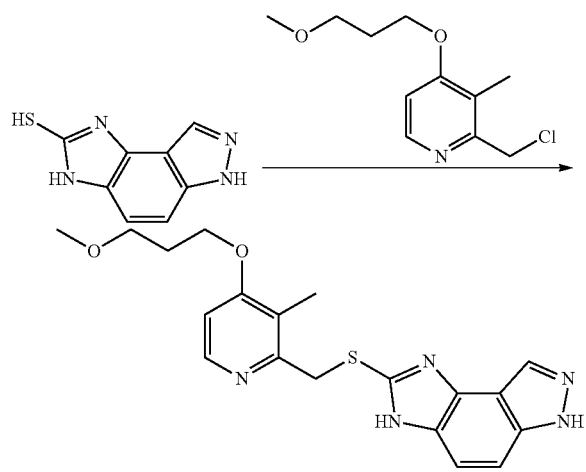

By referring to the Step 8 of Example 1, 2-mercapto-1H,6H-imidazole[4,5-e]indazole (1.5 g, 7.9 mmol), NaOH (0.78 g, 19.5 mmol), 2-(chloromethyl)-4-(3-methoxylpropoxy)-3-methylpyridine (1.8 g, 7.9 mmol), were used to obtain a product (1.8 g, 59.4%).

Step 8: Preparation of Compound 5

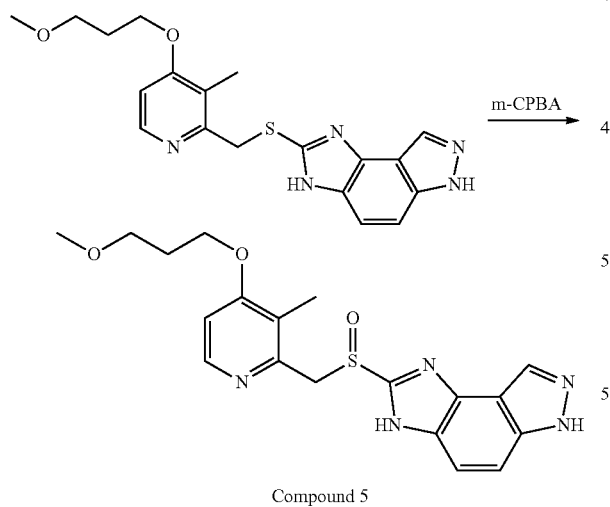

Compound 5

By referring to the Step 9 of Example 1, 2-[[4-(3-methoxylpropoxy)-3-methylpyridin-2-yl]methylsulfo]-3,6-dihydroimidazo[4,5-e]indazole (1.8 g, 4.7 mmol), m-CPBA (0.81 g, 4.7 mmol), were used to obtain a product (1.7 g, 92.8%).

Molecular formula: $C_{19}H_{21}N_5O_3S$; Molecular weight: 399.47; MS: 400 (M+H$^+$)

$^1$H-NMR (CDCl$_3$, 300 MHz) δ: 2.05 (2H, m), 2.22 (3H, s), 3.35 (3H, s), 3.50 (2H, t), 4.05 (2H, t), 4.85 (2H, dd), 6.69 (1H, d), 7.86 (1H, d), 7.52 (1H, d), 8.33 (1H, d), 8.72 (1H, s), 12.89 (1H, br. s), 13.29 (1H, br. s).

Example 6

Preparation of 2-[[4-(3-methoxylpropoxy)-3-methylpyridin-2-yl]methylsulfinyl]-6,7-dihydro-1H-[1,4]dioxino[2,3-f]benzimidazole (Compound 6)

Step 1: Preparation of 6-acetylamino-2,3-dihydrobenzo[b][1,4]dioxane

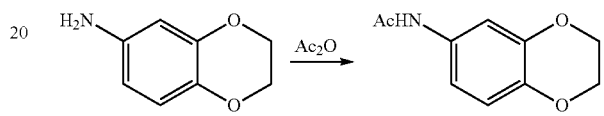

6-amino-2,3-dihydrobenzo[b][1,4]dioxane (9 g, 60 mmol) and acetic anhydride (150 mL) were stirred at room temperature for 3 h, added to ice, extracted with dichloromethane (300 mL). The organic layer was dried, filtered, concentrated under vacuum to obtain a product (10.6 g, 91%).

Step 2: Preparation of 6-acetylamino-7-nitro-2,3-dihydrobenzo[b][1,4]dioxane

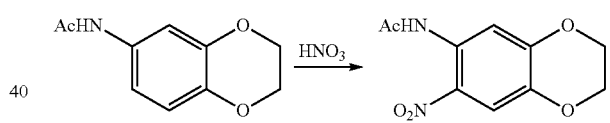

At 0° C., the product obtained in the Step 1 (12.5 g, 65 mmol) was dissolved in acetic acid (100 mL), a concentrated HNO$_3$ (100 mL) was added dropwise, stirred at room temperature for 3 h. The reaction mixture was added to ice-water, adjusted by adding NaOH solution to adjust pH to be 8-9, extracted with dichloromethane. The organic layer was dried, filtered, concentrated under vacuum to obtain a product (13 g, 84%).

Step 3: Preparation of 6-amino-7-nitro-2,3-dihydrobenzo[b][1,4]dioxane

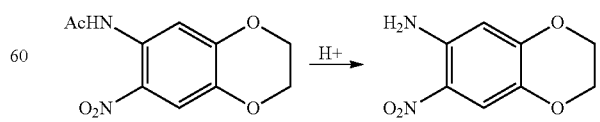

To the product obtained in the Step 2 (13 g, 55 mmol), 2 mol/L H$_2$SO$_4$ solution (500 mL) was added, stirred under refluxing for 6 h. The heat source was removed, the reaction mixture was cooled to 0° C., filtered, washed with water, dried, concentrated under vacuum to obtain a product (8.4 g, 79%).

Step 4: Preparation of 6,7-diamino-2,3-dihydrobenzo[b][1,4]dioxane

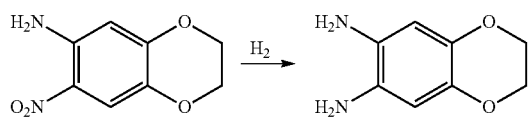

The product obtained in the Step 3 (8.2 g, 42 mmol) was dissolved in anhydrous methanol (300 mL), 10% Pd/C (0.8 g) was added under hydrogen gas pressure, reacted for 18 h. The catalyst was removed by filtration, the filtrate was concentrated under vacuum, diluted with ethyl acetate, and washed with water, dried, concentrated under vacuum to obtain a product (5 g, 72%).

Step 5: 7-mercapto-6H-2,3-dihydro[1,4]dioxino[2,3-d]benzo[d]imidazole

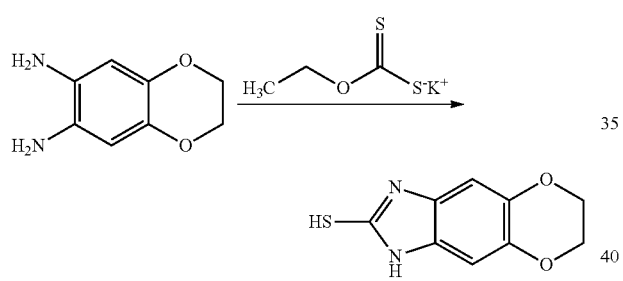

The production obtained in the Step 4 (5 g, 30 mmol) was dissolved in anhydrous methanol (300 mL). Potassium ethylxanthate (7.1 g, 45 mmol) was added, stirred for 5 h. The solvent was removed, water and concentrated hydrochloric acid were added, and the reaction mixture was adjusted to pH 3, and extracted with ethyl acetate. The organic layers were combined and then washed with water and saline, dried, concentrated under vacuum to obtain a product (4.3 g, 69%).

Step 6: Preparation of 2-[[4-(3-methoxylpropoxy)-3-methylpyridin-2-yl]methylsulfo]-6,7-dihydro-1H-[1,4]dioxino[2,3-f]benzimidazole

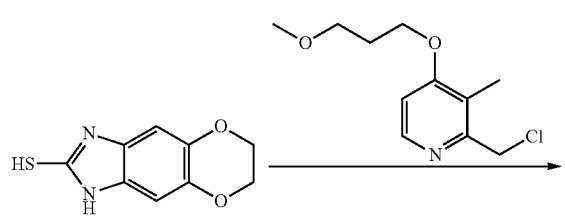

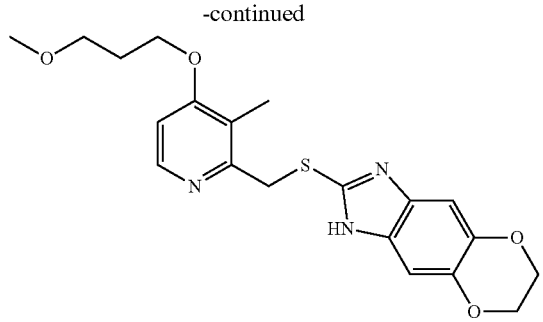

The product of the Step 5 (4.3 g, 20.7 mmol) and NaOH (2.1 g, 51.8 mmol) were dissolved in acetone (20 mL) and water (20 mL), stirred, a solution of 2-(chloromethyl)-4-(3-methoxylpropoxy)-3-methylpyridine (5.5 g, 20.7 mmol) and water (20 mL) were added dropwise at 15-20° C. After filtration at 25-30° C., the filter cake was washed with acetone and water (v:v=1:1), dried to obtain a product (5 g, 60%).

Step 7: Preparation of Compound 6

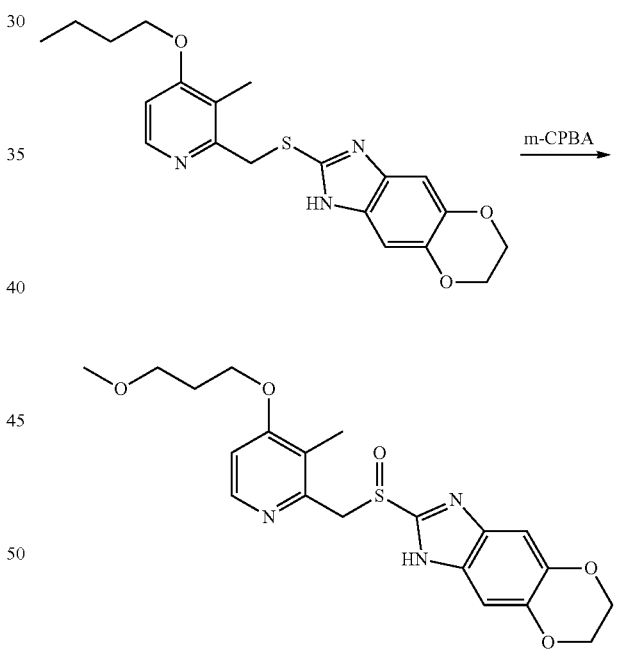

Compound 6

The product obtained in the Step 6 (3 g, 7.5 mmol) was dissolved in dichloromethane (200 mL), stirred, m-chloroperbenzoic acid m-CPBA (1.2 g, 7.5 mmol) was added in 3 batches at −50° C. within 1.5 h. The reaction mixture was added into saturated $NaHCO_3$, extracted with dichloromethane, the organic layers were combined and then washed with saline, dried, concentrated under vacuum, purified by column chromatography to obtain a product (2.8 g, 89%).

Step 8: Preparation of Sodium Salt of Compound 6

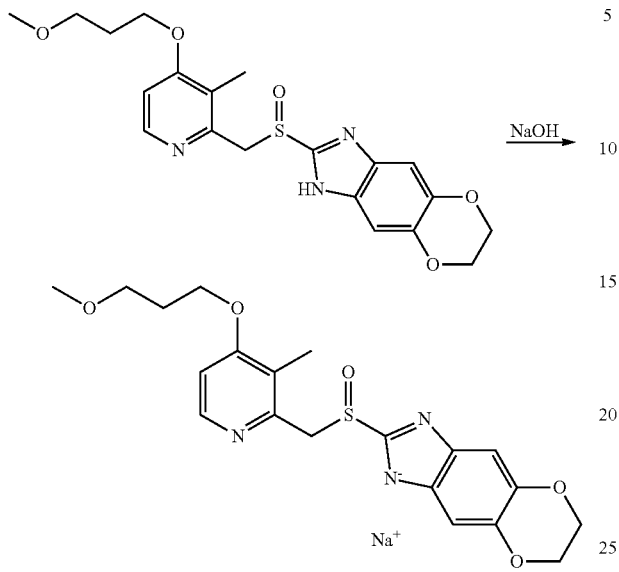

The product obtained in the Step 7 (13 g, 55 mmol) was added to 0.1 mol/L NaOH solution (20 mL), stirred at room temperature for 1 h, diluted with dichloromethane, washed with saturated saline, dried, concentrated under vacuum, purified by production HPLC to obtain a product (0.5 g, 39%).

Molecular formula: $C_{20}H_{22}N_3NaO_5S$; Molecular weight: 439.46; MS: 418 (M+H$^+$)

$^1$H-NMR (CDCl$_3$, 400 MHz) δ: 2.08 (2H, m), 2.19 (3H, s), 3.36 (3H, s), 3.55 (2H, t), 4.10 (2H, t), 4.30 (4H, t), 4.66 (1H, d), 4.78 (1H, d), 6.74 (1H, d), 7.10 (1H, s), 7.13 (1H, s), 8.31 (1H, d).

Example 7

Preparation of 2-[[4-(3-methoxylpropoxy)-3-methylpyridin-2-yl]methylsulfinyl]-1H,5H-imidazo[5,4-f]benzo[d]imidazole (Compound 7)

Step 1: Preparation of 5,6-dinitro-1H-benzo[d]imidazole

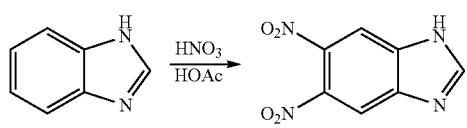

Benzimidazole (5 g, 42.3 mmol) was dissolved in 35 mL acetic acid, ¼ concentrated HNO$_3$ (0.9 mL, 45.4 mmol) was added dropwise. At the beginning, the reaction was heated to 70° C., then the residual HNO$_3$ was added. After half an hour, the reaction was cooled, added to ice-water, neutralized with Na$_2$CO$_3$. The water layer was extracted with ethyl acetate. The combined organic layers were dried, concentrated under vacuum, purified by column chromatography to obtain a product (1.4 g, 15.7%).

Step 2: Preparation of 5,6-diamino-1H-benzo[d]imidazole

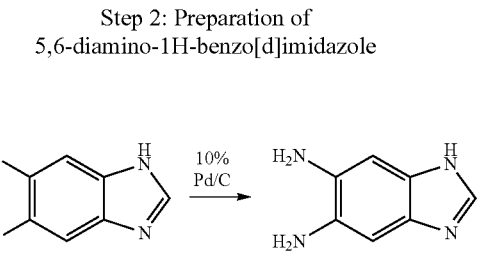

The product obtained in Step 1 (2.5 g, 12 mmol) and Pd/C (0.5 g) were dissolved in EtOH (50 mL), reacted in a Parr hydrogenation apparatus at room temperature and hydrogen gas pressure until the reaction is completed. The catalyst was removed by filtration, the filtrate was concentrated under vacuum, diluted with ethyl acetate, washed with water, dried, and concentrated under vacuum to obtain a product (1.2 g, 66.7%).

Step 3: Preparation of 2-mercapto-1H,5H-imidazo[5,4-f]benzo[d]imidazole

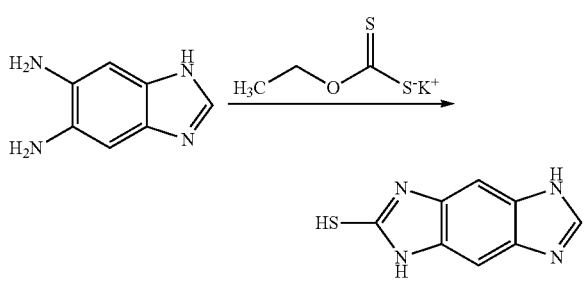

The product obtained in the Step 2 (2 g, 13.4 mmol) was dissolved in anhydrous ethanol (50 mL). Potassium ethylxanthate (3.2 g, 20 mmol) was added, stirred for 5 h. The solvent was removed, water and concentrated hydrochloric acid were added, and the reaction mixture was adjusted to pH 3, and extracted with ethyl acetate. The organic layers were combined and washed with water and saline, dried, concentrated under vacuum to obtain a product (1.4 g, 53.4%).

Step 4: Preparation of 2-[[4-(3-methoxylpropoxy)-3-methylpyridin-2-yl]methylsulfo]-1H,5H-imidazo[5,4-t]benzo[d]imidazole

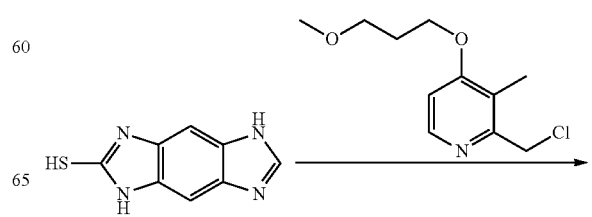

-continued

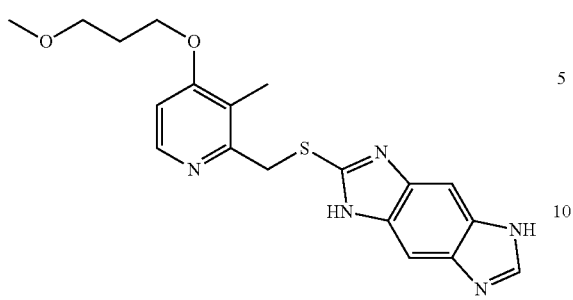

The product obtained in the Step 3 (1.3 g, 6.8 mmol) and NaOH (0.68 g, 17 mmol) were dissolved in acetone (10 mL) and water (10 mL), stirred, and added with 2-(chloromethyl)-4-(3-methoxylpropoxy)-3-methylpyridine (1.6 g, 6.8 mmol), stirred at room temperature, filtered. The filter cake was washed with acetone and water (v:v=1:1), dried to obtain a product (1.4 g, 51.9%).

Step 5: Preparation of Compound 7

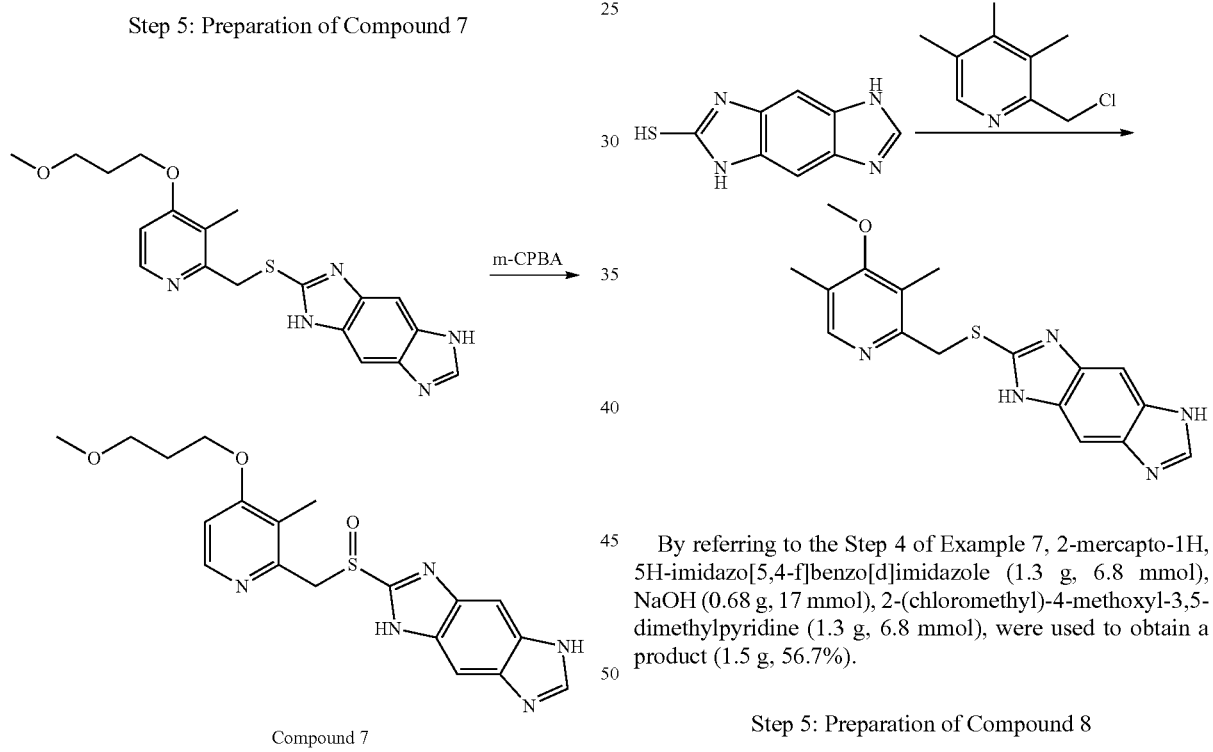

Compound 7

The product obtained in the Step 4 (1.4 g, 3.65 mmol) was dissolved in dichloromethane (20 mL), stirred at −78° C., m-chloro-perbenzoic acid m-CPBA (0.63 g, 3.65 mmol) was added in 3 batches within 1 h. The reaction mixture was added to saturated NaHCO₃, extracted with dichloromethane, the organic layers were combined and washed with saline, dried, concentrated under vacuum, purified by column chromatography to obtain a product (1.3 g, 90.6%).

Molecular formula: $C_{19}H_{21}N_5O_3S$; Molecular weight: 399.47; MS: 400 (M+H⁺)

¹H-NMR (CDCl₃, 500 MHz) δ: 1.98 (2H, m), 2.17 (3H, s), 3.25 (3H, s), 3.48 (2H, t), 4.10 (2H, t), 4.53 (1H, d), 4.80 (1H, d), 6.94 (1H, d), 7.65 (2H, s), 8.08 (1H, s), 8.28 (1H, d), 12.9 (1H, s), 13.2 (1H, s).

Example 8

Preparation of 2-[(3,5-dimethyl-4-methoxylpyridin-2-yl)methyl-sulfinyl]-1H,5H-imidazo[5,4-d]benzo[d]imidazole (Compound 8)

Step 1 to Step 3 were performed by referring to the Step 1 to Step 3 of Example 7.

Step 4: Preparation of 2-[(3,5-dimethyl-4-methoxylpyridin-2-yl)methylsulfo]-1H,5H-imidazo[5,4-f]benzo[d]imidazole By referring to the Step 4 of Example 7, 2-mercapto-1H,5H-imidazo[5,4-f]benzo[d]imidazole (1.3 g, 6.8 mmol), NaOH (0.68 g, 17 mmol), 2-(chloromethyl)-4-methoxyl-3,5-dimethylpyridine (1.3 g, 6.8 mmol), were used to obtain a product (1.5 g, 56.7%).

Step 5: Preparation of Compound 8

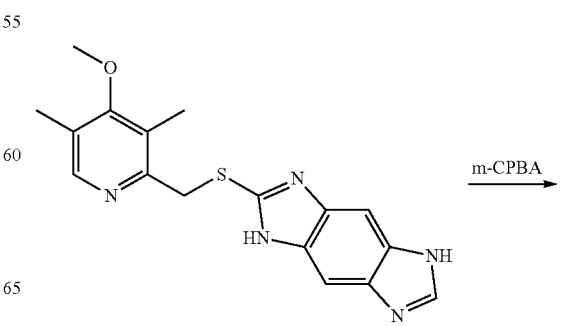

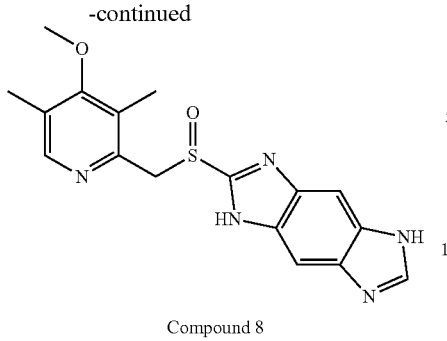

Compound 8

By referring to the Step 5 of Example 7, 2-[(3,5-dimethyl-4-methoxylpyridin-2-yl)methylsulfo]-1H,5H-imidazo[5,4-f]benzo[d]imidazole (1.2 g, 3.65 mmol), m-CPBA (0.63 g, 3.65 mmol), were used to obtain a product (1.2 g, 89.4%).

Molecular formula: $C_{17}H_{17}N_6O_2S$; Molecular weight: 355.41 MS: 356 (M+H$^+$)

$^1$H-NMR (DMSO-d$_6$, 300 MHz) δ: 2.15 (3H, s), 2.18 (3H, s), 3.66 (3H, s), 4.75 (2H, dd), 7.58-7.89 (2H, m), 8.10 (1H, s), 8.29 (1H, s), 12.40 (1H, s), 13.30 (1H, br. s).

Example 9

Preparation of 2-[[3-methyl-4-(2,2,2-trifluoroethoxyl)pyridin-2-yl]methylsulfinyl]-1H,5H-imidazo[5,4-d]benzo[d]imidazole (Compound 9)

Step 1 to Step 3 were performed by referring to the Step 1 to Step 3 of Example 7.

Step 4: Preparation of 2-[[3-methyl-4-(2,2,2-trifluoroethoxyl)pyridin-2-yl]methylsulfo-1H,5H-imidazo[5,4-d]benzo[d]imidazole

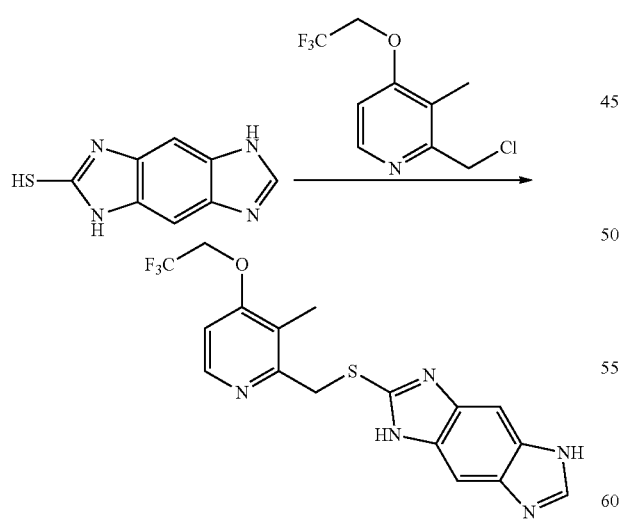

By referring to the Step 4 of Example 7, 2-mercapto-1H,5H-imidazo[5,4-f]benzo[d]imidazole (1.3 g, 6.8 mmol), NaOH (0.68 g, 17 mmol), 2-(chloromethyl)-3-methyl-4-(2,2,2-trifluoroethoxyl)pyridine (1.6 g, 6.8 mmol), were used to obtain a product (1.5 g, 54.9%).

Step 5: Preparation of Compound 9

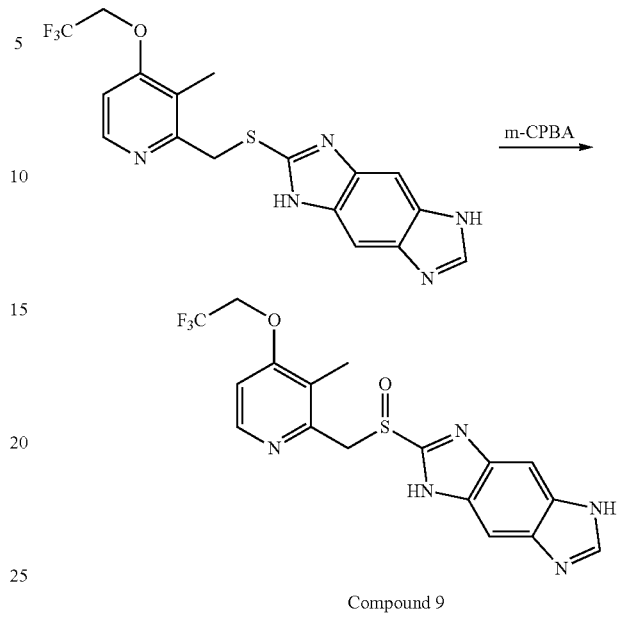

Compound 9

By referring to the Step 5 of Example 7, 2-[[3-methyl-4-(2,2,2-trifluoroethoxyl)pyridin-2-yl]methylsulfo]-1H,5H-imidazo[5,4-f]b enzo[d]imidazole (1.4 g, 3.65 mmol), m-CPBA (0.63 g, 3.65 mmol), were used to obtain a product (1.3 g, 88.6%).

Molecular formula: $C_{17}H_{14}F_3N_6O_2S$; Molecular weight: 409.39; MS: 410 (M+H$^+$)

$^1$H-NMR (DMSO-d$_6$, 300 MHz) δ: 2.16 (3H, s), 4.80 (2H, dd), 4.91 (2H, t), 7.05 (1H, d), 7.60-7.79 (2H, m), 8.25 (1H, d), 8.26 (1H, s), 12.3 (1H, d), 13.3 (1H, m).

Example 10

Preparation of 2-[(3,4-dimethoxylpyridin-2-yl)methylsulfinyl]-1H,5H-imidazo[5,4-d]benzo[d]imidazole (Compound 10)

Step 1 to Step 3 were performed by referring to the Step 1 to Step 3 of Example 7.

Step 4: Preparation of 2-[(3,4-dimethoxylpyridin-2-yl)methylsulfo]-1H,5H-imidazo[5,4-t]benzo[d]imidazole

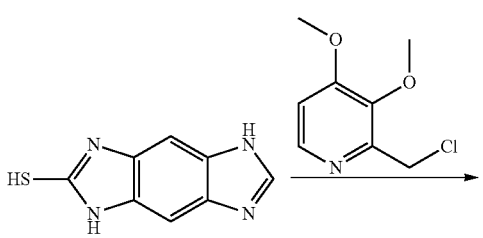

-continued

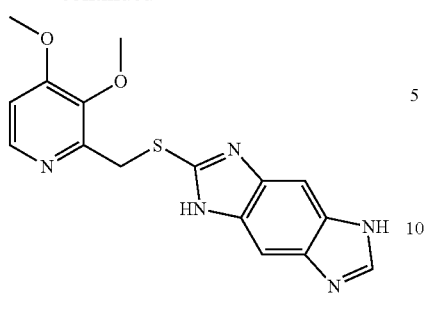

By referring to the Step 4 of Example 7, 2-mercapto-1H, 5H-imidazo[5,4-f]benzo[d]imidazole (1.3 g, 6.8 mmol), NaOH (0.68 g, 17 mmol), 2-chloromethyl-3,4-dimethoxylpyridine (1.3 g, 6.8 mmol), were used to obtain a product (1.5 g, 64.7%).

Step 5: Preparation of Compound 10

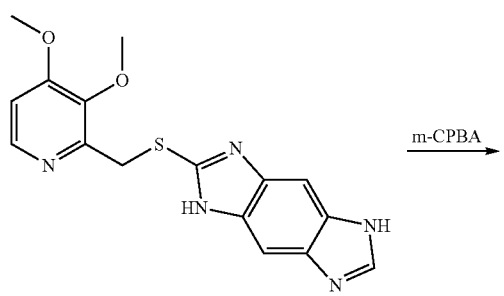

By referring to the Step 5 of Example 7, 2-(3,4-dimethoxylpyridin-2-yl)methylsulfo-1H,5H-imidazo[5,4-t]benzo[d]imidazole (1.2 g, 3.65 mmol), m-CPBA (0.63 g, 3.65 mmol), were used to obtain a product (1.2 g, 94.6%).

Molecular formula: $C_{16}H_{16}N_6O_3S$; Molecular weight: 357.39 MS: 358 (M+H$^+$)

$^1$H-NMR (DMSO-d$_6$, 300 MHz) δ: 3.75 (3H, s), 3.88 (3H, s), 4.66 (2H, dd), 7.09 (1H, s), 7.72 (1H, s), 7.66 (1H, s), 8.14 (1H, s), 8.25 (1H, s), 12.32 (1H, s), 13.34 (1H, br. s).

Example 11

Preparation of 6-[[4-(3-methoxylpropoxy)-3-methylpyridin-2-yl]methylsulfinyl]-1,5-dihydro-imidazo[4,5-f]indazole (Compound 11)

Step 1: Preparation of 5,6-dinitroindazole

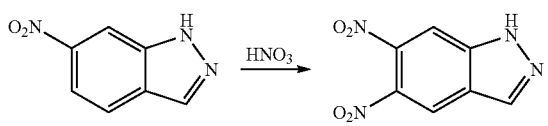

By referring to the Step 1 of Example 7, 6-nitroindazole (5 g, 30.7 mmol), 35 mL of acetic acid, concentrated HNO$_3$ (3.6 mL, 181.6 mmol), were used to obtain a product (1.8 g, 28.6%).

Step 2: Preparation of 5,6-diaminoindazole

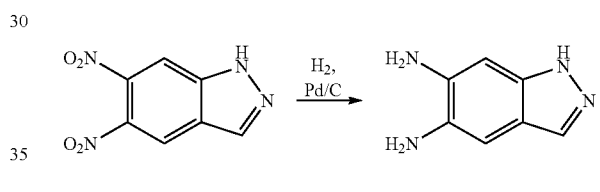

By referring to the Step 2 of Example 7, 5,6-dinitroindazole (5.0 g, 24.0 mmol), 10% Pd/C (1 g), were used to obtain a product (2.4 g, 66.7%).

Step 3: Preparation of 6-mercapto-1H,5H-imidazo[4,5-t]indazole

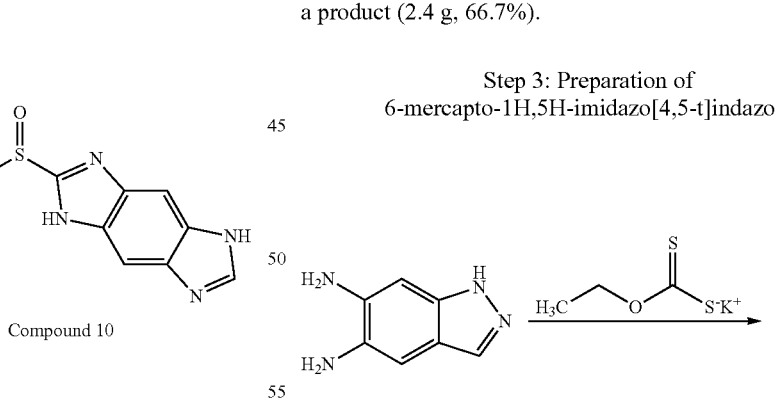

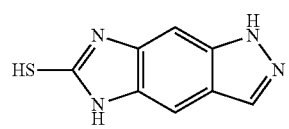

By referring to the Step 3 of Example 7, 5,6-diaminoindazole (2.4 g, 16.2 mmol), potassium ethylxanthate (4.0 g, 25 mmol), were used to obtain a product (1.9 g, 62.8%).

Step 4: Preparation of 6-[[4-(3-methoxylpropoxy)-3-methylpyridin-2-yl]methylsulfo]-1,5-dihydro-imidazo[4,5-f]indazole

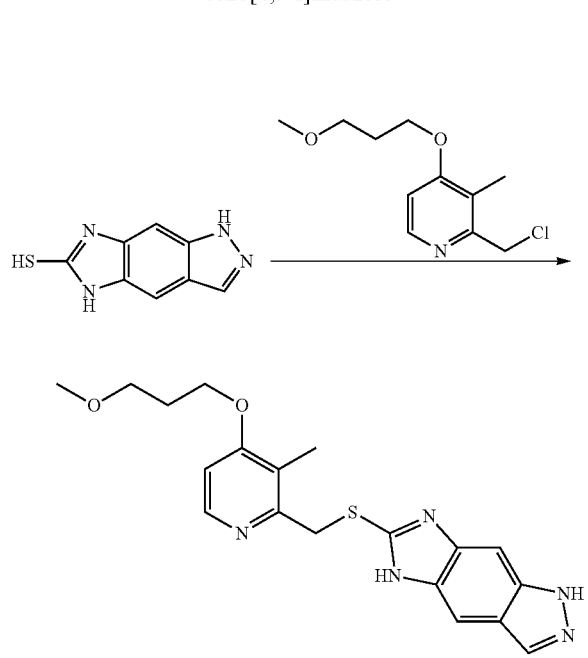

By referring to the Step 4 of Example 7, 6-mercapto-1H, 5H-imidazo[4,5-t]indazole (1.3 g, 6.8 mmol), NaOH (0.68 g, 17 mmol), 2-(chloromethyl)-4-(3-methoxylpropoxy)-3-methylpyridine (1.6 g, 6.8 mmol), were used to obtain a product (1.5 g, 57.5%).

Step 5: Preparation of Compound 11

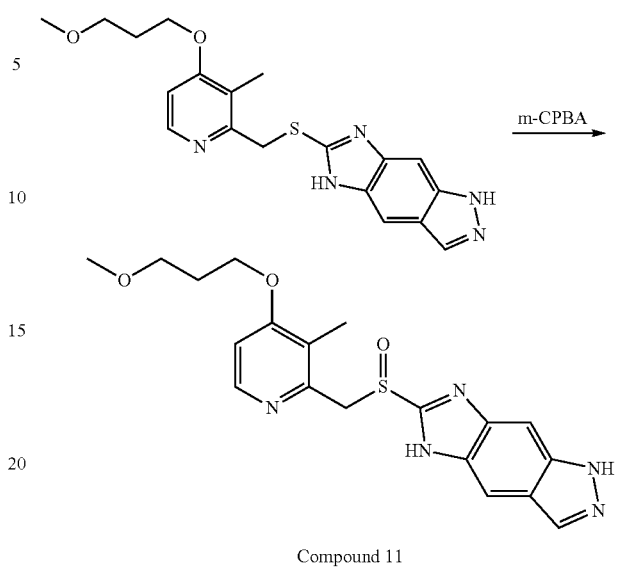

Compound 11

By referring to the Step 5 of Example 7, 6-[[4-(3-methoxylpropoxy)-3-methylpyridin-2-yl]methylsulfo]-1,5-dihydro-imidazo[4,5-f]indazole (1.5 g, 3.9 mmol), m-CPBA (0.63 g, 3.9 mmol), were used to obtain a product (1.4 g, 92.5%).

Molecular formula: $C_{19}H_{21}N_5O_3S$; Molecular weight: 399.47; MS: 400 (M+H$^+$)

$^1$H-NMR (CDCl$_3$, 500 MHz) δ: 1.98 (2H, m), 2.17 (3H, s), 3.25 (3H, s), 3.49 (2H, t), 4.09 (2H, t), 4.71 (1H, d), 4.80 (1H, d), 6.93 (1H, d), 7.52 (1H, s), 8.07 (1H, s), 8.18 (1H, s), 8.28 (1H, d), 12.83 (1H, s); 13.28 (1H, s).

The following compounds were also prepared by using the above methods:

TABLE 2

| No. | Structural formula | MS |
|---|---|---|
| 12 | | 356(M + H)$^+$ |
| 13 | | 402(M + H)$^+$ |

Exemplary compounds of the present invention

TABLE 2-continued

Exemplary compounds of the present invention

| No. | Structural formula | MS |
|---|---|---|
| 14 | | 412(M + H)+ |
| 15 | | 374(M + H)+ |
| 16 | | 428(M + H)+ |
| 17 | | 356(M + H)+ |
| 18 | | 400(M + H)+ |

TABLE 2-continued

Exemplary compounds of the present invention

| No. | Structural formula | MS |
|---|---|---|
| 19 | | 378(M + H)+ |
| 20 | | 356(M + H)+ |
| 21 | | 342(M + H)+ |
| 22 | | 358(M + H)+ |
| 23 | | 402(M + H)+ |

TABLE 2-continued
Exemplary compounds of the present invention
| No. | Structural formula | MS |
|---|---|---|
| 24 | 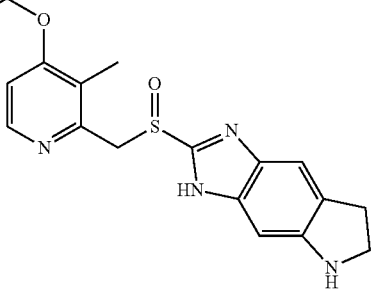 | 401(M + H)+ |
| 25 | 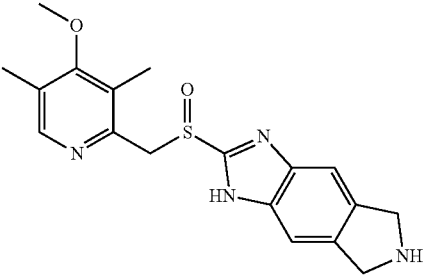 | 366(M + H)+ |
| 26 | 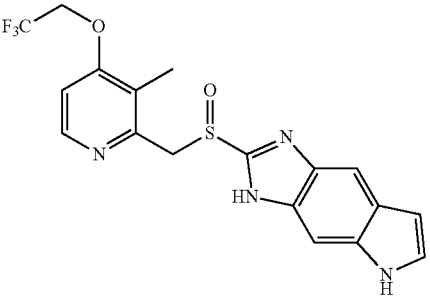 [SMILES: Cc1c(OCC(F)(F)F)ccnc1CS(=O)c1nc2cc3cc[nH]c3cc2[nH]1] | 409(M + H)+ |
| 27 | 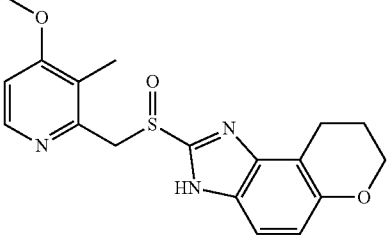 | 416(M + H)+ |
| 28 | 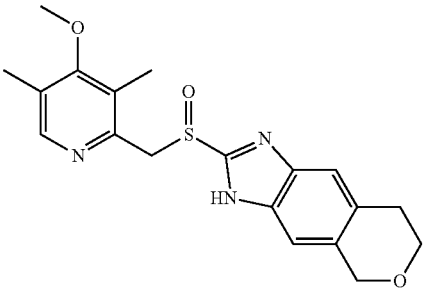 | 372(M + H)+ |

Example 12

Preparation of (S)-2-[[[4-(3-methoxylpropoxy)-3-methyl-2-pyridyl]methyl]-sulfinyl]-6,7-dihydro-3H-benzofuro[5,6-d]imidazole (Compound 29)

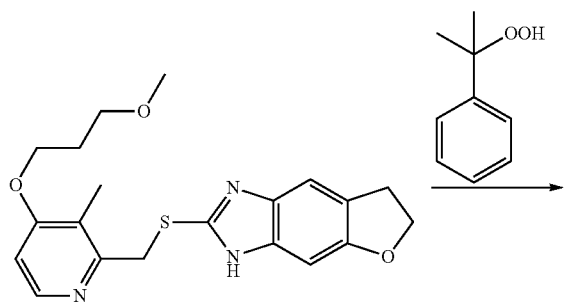

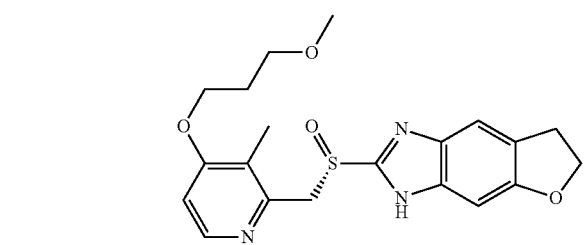

A mixture of 2-[[4-(3-methoxylpropoxy)-3-methylpyridin-2-yl]methylsulfo]-6,7-dihydro-3H-benzofuro[5,6-d]imidazole (the compound obtained in the Step 8 of Example 1) (48 g, 125 mmol), toluene (300 mL), D-(–)-diethyl tartrate (32.3 mL, 188 mmol), tetraisopropyl titanate (22.2 mL, 75 mmol) and deionized water (0.8 mL, 44 mmol) was stirred at 55° C. for 1 h, cooled to 10° C., added with N,N-diisopropylethylamine (8.9 mL, 54 mmol), then cumyl hydroperoxide (23.3 mL, 137 mmol) was added dropwise to the reaction solution, stirred for 12 h. Aqueous ammonia (12.5%) was used for extraction, and the aqueous phase was adjusted with glacial acetic acid to pH=8, filtered, washed with water, dried, and recrystallized to obtain a product (14 g, 28%).

Example 13

Preparation of (R)-2-[[[4-(3-methoxylpropoxy)-3-methyl-2-pyridyl]methyl]-sulfinyl]-6,7-dihydro-3H-benzofuro[5,6-d]imidazole (Compound 30)

CHIRALPAK AS-H was used as analytical column (silica surface was coated with amylose-tri{(S)-α-tolylphenylcarbamate} as stationary phase); the mobile phase was n-hexane-ethanol-diethylamine (50:50:0.1) (v/v/v); Compound 29 and Compound 30 was obtained by resolution of Compound 1.

Example 14

Preparation of 2-[[[4-(3-methoxylpropoxy)-3-methyl-2-pyridyl]methyl]-sulfinyl]-6,7-dihydro-3H-benzofuro[5,6-d]imidazole sodium (sodium salt of Compound 30)

Step 1: Preparation of 5-nitro-2,3-dihydrobenzofuran

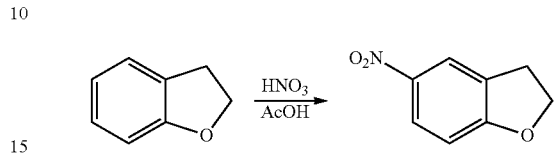

2,3-Dihydrobenzofuran (36 g, 0.3 mol) was added to glacial acetic acid (100 mL), heated to 65° C., then concentrated nitric acid (25 mL, 0.36 mol) was added dropwise into the reaction solution, the temperature of the reaction solution was controlled at 65-75° C. After the end of dropwise addition, the agitation was kept for 0.5 h. It was then cooled to room temperature, filtered, washed with water, and dried to obtain a product (22 g, 44.4%).

Step 2: Preparation of 5-amino-2,3-dihydrobenzofuran

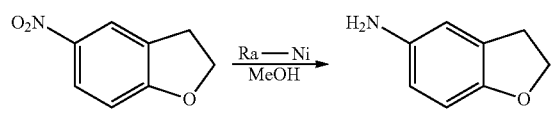

A mixture of the product obtained in the Step 1 (15 g, 91 mmol), Pd/c (1.5 g) and anhydrous ethanol (50 mL) reacted at 50° C. and 2 MPa hydrogen gas for 3 h, filtrated, and concentrated to obtain a product (11.2 g, 91.1%).

Step 3: Preparation of 5-amino-6-nitro-2,3-dihydrobenzofuran

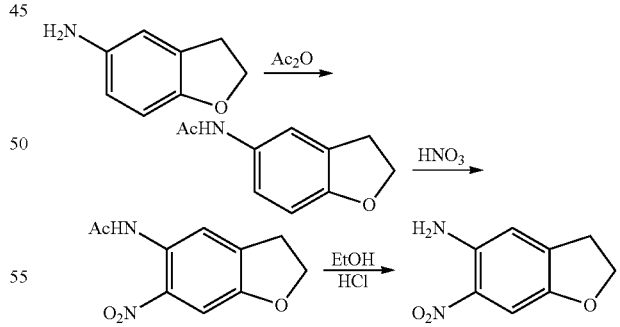

At room temperature, acetic anhydride (10.3 mL, 110 mmol) was added dropwise to a solution of the product obtained in the Step 2 (12 g, 89 mmol) and ethyl acetate (80 mL), after dropwise addition, acetic anhydride (19 mL) was further added, stirred for 0.5 h. Then concentrated nitric acid (7.6 mL, 110 mmol) was added dropwise into the above reaction solution, cooled to room temperature, filtered to obtain a solid. The reaction mixture of the solid, hydrochloric acid (20 mL) and anhydrous ethanol (40 mL) was refluxed for 4 h, cooled to room temperature, filtrated, washed with water, and dried to obtain a product (9.8 g, 61.3%).

Step 4: Preparation of 2-mercapto-6,7-dihydro-3H-benzofuro[5,6-d]imidazole

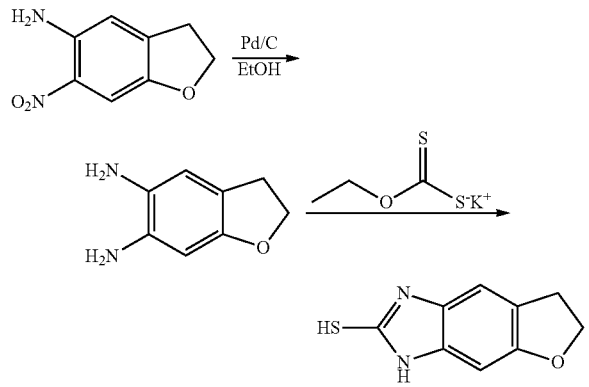

The product obtained in the Step 3 (36 g, 0.2 mol), Pd/C (3.6 g) and anhydrous ethanol (100 mL) were added to a hydrogenation reaction kettle, reacted at 50° C., 4 MPa hydrogen gas pressure for 2 h, filtrated.

The mixture of the filtrate and potassium ethylxanthate (35.2 g, 0.22 mol) was refluxed for 4 h, cooled to room temperature, filtered, washed with water and ethanol in sequence, dried to obtain a product (34 g, 88.5%).

Step 5: Preparation of 2-[[4-(3-methoxylpropoxy)-3-methyl-2-pyridyl]methylsulfo]-6,7-dihydro-3H-benzofuro[5,6-d]imidazole

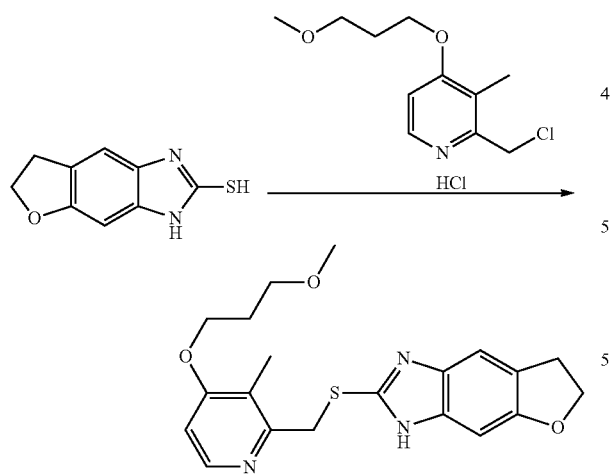

A solution of 2-chloromethyl-4-(3-methoxylpropoxy)-3-methylpyridine hydrochloride (26.6 g, 0.1 mol) and anhydrous methanol (100 mL) was added dropwise to a mixture of the product as obtained in the Step 4 (19.2 g, 0.1 mol), sodium hydroxide (8 g, 0.2 mol) and anhydrous methanol (100 mL), after the end of dropwise addition, the agitation was kept for 3 h, then concentrated, filtered, washed with water, dried and recrystallized to obtain a product (27 g, 70.1%).

Step 6: Preparation of (R)-2-[[[4-(3-methoxylpropoxy)-3-methyl-2-pyridyl]methyl]sulfinyl]-6,7-dihydro-3H-benzofuro[5,6-d]imidazole (Compound 30)

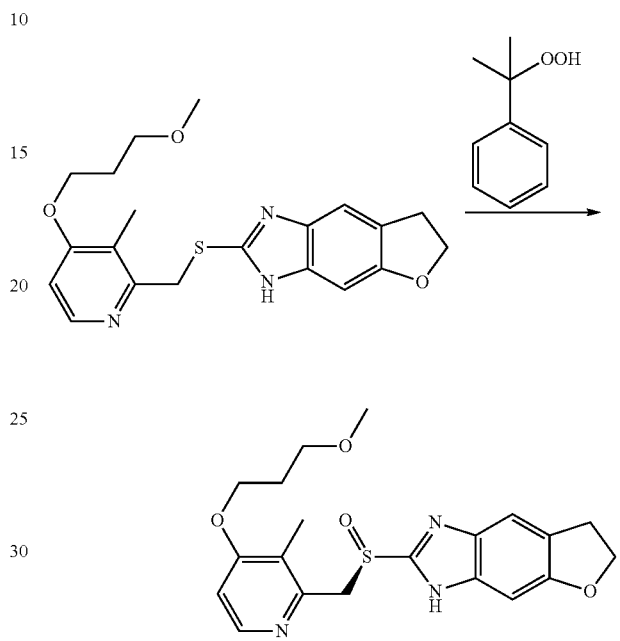

A mixture of the product obtained in the Step 5 (48 g, 125 mmol), toluene (300 mL), L-(+)-tartaric acid diethyl ester (32.3 mL, 188 mmol), tetraisopropyl titanate (22.2 mL, 75 mmol) and deionized water (0.8 mL, 44 mmol) was stirred at 55° C. for 1 h, cooled to 10° C., added with N,N-diisopropylethylamine (8.9 mL, 54 mmol), then cumyl hydroperoxide (23.3 mL, 137 mmol) was added dropwise to the reaction solution, stirred for 12 h, extracted with aqueous ammonia (12.5%), the aqueous phase was adjusted with glacial acetic acid to pH=8, filtered, washed with water, dried, and recrystallized to obtain a product (14 g, 28%).

Step 7: Preparation of (R)-2-[[[4-(3-methoxylpropoxy)-3-methyl-2-pyridyl]methyl]sulfinyl]-6,7-dihydro-3H-benzofuro[5,6-d]imidazole sodium

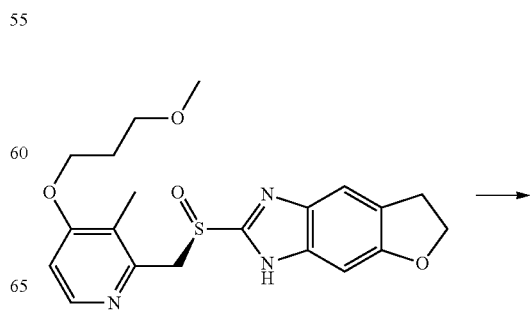

-continued

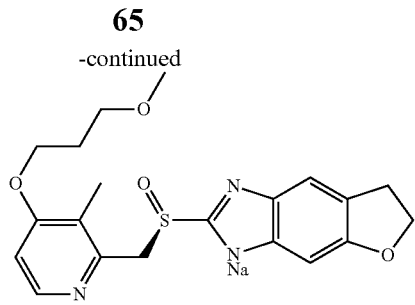

At 40° C., the product obtained in the Step 6 (10 g, 25 mmol) was dissolved in acetonitrile (50 mL), and then aqueous solution of sodium hydroxide (2.1 g, 47%) was added dropwise into the above solution. After the end of dropwise addition, stirred for 30 min, cooled to room temperature, further stirred for 1 h, stood at 0° C. for 2 h, filtered, washed with ethyl ether, dried under vacuum at 40° C. to obtain a product (9.5 g, 90.0%).

Molecular formula: $C_{20}H_{22}N_3NaO_4S$; Molecular weight: 423.46; MS: 402 $(M+H^+)$ $^1$H-NMR (400 MHz, DMSO-$d_6$) δ: 1.98 (2H, m), 2.15 (3H, s), 3.18 (2H, t), 3.25 (3H, s), 3.48 (2H, t), 4.09 (2H, t), 4.37 (1H, d), 4.44 (2H, t), 4.72 (1H, d), 6.75 (1H, s), 6.92 (1H, d), 7.27 (1H, s), 8.27 (1H, d).

Experimental Example 1

Inhibition Effects of the Compounds of the Present Invention on Gastric Acid in Pylorus Ligated Rats 1. Experimental Materials Experimental animals: six-week old clean Wistar rats, male, 140-180 g.

Experimental samples: part of the compounds of the present invention, which structural formula and chemical name are shown in Table 1. Compound 81 was used as contrast compound, which structural formula is shown in the "Background is Art" section. Before test, these compounds were dissolved with physiological saline.

2. Experimental Methods

After the rats of all groups were fasted without water deprivation for 48 h, they were etherized, and incised at subxiphoid abdomen midline to expose gastric wall. Pylorus was ligated by passing a suture beneath gastric pylorus, the drugs were immediately administered through duodenum, in which the solvent group was administered with physiological saline in 2 mL/kg, and the test sample groups were administered with corresponding test samples in 20 mg/kg. The animals were executed after 6 h, laparotomized, esophagus was ligated near to diaphragmatic muscle, whole stomach was taken out, washed to remove blood, stomach contents were poured out, the acidity degree of gastric acid was tested with pH test paper, the stomach contents was then centrifuged at 3000 rpm for 10 min. The volume of the supernatant was metered, and 1 mL of the supernatant was titrated with 0.01 mol/L NaOH solution, phenolphthalein was used as indicator, the volume of NaOH was recorded, and the total acidity degree and total acid output of gastric juice were calculated.

Gastric juice total acidity degree (mmol/L)=consumed volume of NaOH solution (mL)*0.01 mol/L (NaOH concentration)/1 mL (supernatant volume)*1000;

1 h total acid output (mmol/h)=total acidity degree (mmol/L)*gastric juice volume (mL)/6 h/1000.

3. Experimental Results

The Experimental results are shown in form of average value±standard deviation, and the data are treated with t-test. The specific test results are shown in Table 3.

TABLE 3

| | | Gastric juice total acidity degree and total acid output | | | |
|---|---|---|---|---|---|
| Group | Animals (number) | Acidity degree (pH value) | Gastric juice volume (mL) | Total acidity degree (mmol/L) | Total acid output (mmol/h) |
| Solvent | 3 | 2.0 ± 1.00 | 4.50 ± 0.46 | 104.37 ± 10.58 | 0.0789 ± 0.0147 |
| Compound 1 (sodium salt) | 7 | 3.14 ± 1.31 | 3.33 ± 0.97 | 47.85 ± 24.38 | 0.0276 ± 0.0194 |
| Compound 6 (sodium salt) | 6 | 1.82 | 10.28 | 103.16 | 0.0807 |
| Compound 8 | 6 | 1.71 | 6.10 | 120.92 | 0.1242 |

4. Conclusion

In comparison with the solvent group, the group of Compound 1 of the present invention has a significantly increase in acidity degree and pH value of gastric acid, and a decrease or significant decrease in gastric juice volume, total acidity degree of gastric juice, total acid output, which indicate Compound 1 of the present invention has a significant inhibition effect on the gastric acid secretion in pylorus ligated rats. The group of Compound 6 and the group of Compound 8 do not show inhibition effect on the gastric acid secretion in pylorus ligated rats.

5. Referring to Experimental Example 1, the compounds of the present invention were separately administered in a dose of 30 mg/kg, the solvent group was administered with the same volume of solvent (2 mL/kg). The test results are shown in Table 4.

TABLE 4

Total acidity degree and total acid output of gastric juice

| Group | Animals (number) | Acidity degree (pH value) | Gastric juice volume (mL) | Volume of supernatant of gastric juice (mL) | Total acidity degree (mmol/L) | Total acid output (mmol/h) |
|---|---|---|---|---|---|---|
| Solvent | 6 | 1.42 ± 1.02 | 4.75 ± 2.28 | 4.28 ± 2.42 | 103.02 ± 10.93 | 0.0751 ± 0.0441 |
| Compound 1 (sodium salt) | 5 | 3.90 ± 1.60$^{\triangle\triangle}$ | 3.60 ± 0.88 | 2.92 ± 0.71 | 28.98 ± 7.22$^{\triangle\triangle}$ | 0.0141 ± 0.0051$^{\triangle\triangle}$ |
| Compound 29 | 6 | 3.75 ± 1.13$^{\triangle\triangle}$ | 3.43 ± 1.11 | 2.70 ± 1.04 | 37.85 ± 15.41$^{\triangle\triangle}$ | 0.0178 ± 0.0100$^{\triangle\triangle}$ |
| Compound 30 (sodium salt) | 6 | 6.08 ± 0.92$^{\triangle\triangle}$ ** | 3.60 ± 1.30 | 2.87 ± 1.17 | 17.21 ± 9.34$^{\triangle\triangle}$ | 0.0076 ± 0.0033$^{\triangle\triangle}$ |

In comparison with the solvent group:
$^{\triangle\triangle}$P < 0.01; by comparing the group of Compound 29 and the group of Compound 30 with the group of Compound 1:
**P < 0.01.

6. Referring to Experimental Example 1, the compounds of the present invention, Compound 81 as control were separately administered in a dose of 20 mg/kg, the solvent group was administered with the same volume of solvent (2 mL/kg). The test results are shown in Table 5.

TABLE 5

Gastric juice total acidity degree

| Group | Animals (number) | Total acidity degree (mmol/L) |
|---|---|---|
| Solvent | 5 | 94.46 ± 19.20 |
| Compound 1 (sodium salt) | 5 | 54.52 ± 13.87 |
| Compound 81 as contrast | 5 | 71.27 ± 16.51 |

Experimental Example 2

Test of Effects of the Compounds of the Present Invention on Reflux Esophagitis in Rats 1. Experimental Method:

Wistar rats, half male and half female, were fasted without water deprivation for 26 h, randomly divided into the group of Compound 1, the group of Compound 6, the group of Compound 81 as contrast and the model group, 6 rats per group. The rats were etherized, laparotomized, pylorus ligated, and ligated at the part between glandular stomach and rumen. After ligation, the drugs were immediately administered through duodenum, in which the groups of the test samples were administered with test samples in 20 mg/kg, the model group was administered with the same volume of solvent, and the abdomens were then closed. The rats were released to the fasting cage, subjected to fasting and water deprivation for 5 h and then executed by air embolism. The stomach and esophagus were taken out together, fixed with 1% formaldehyde in esophagus for 1 h, and then the injury of esophagus was observed.

2. Observation of Esophagitis Index

The proportion of esophagitis injury area relative to total esophagus area is used as an esophagitis index, 0 score for no injury, 1 score for injury area of 1-25%, 2 scores for injury area of 25-50%, 3 scores for injury area of 50-75%, and 4 scores for injury area exceeding 75% or perforation.

3. Analytic Method and Results

The experimental results are shown in a form of average value±standard deviation, and esophagitis index data are subjected to Mann-Whitney U test.

TABLE 6

Esophagitis index

| Group | Animals (number) | Esophagitis index |
|---|---|---|
| Model | 6 | 3.17 ± 1.60 |
| Compound 1 (sodium salt) | 6 | 0.00 ± 0.00** |
| Compound 6 (sodium salt) | 6 | 3.00 ± 1.27 |
| Compound 81 as contrast | 6 | 0.83 ± 1.60 |

Notation: in comparison with the model group,
** P < 0.01.

TABLE 7

Injury status for different groups administered with drugs

| Group | Mark | Gender | Esophagus injury score | Injury status |
|---|---|---|---|---|
| Model | Double fore | Female | 4 | Bleeding in a large area of esophageal wall, injury area >75% |
| | Double hind | Female | 4 | Bleeding in a large area of esophageal wall, injury area >75% |
| | Left fore and hind | Female | 4 | Esophageal perforation |
| | Double fore | Male | 4 | Bleeding in a large area of esophageal wall, injury area >75% |
| | Double hind | Male | 3 | Ulcer bleeding, injury area <75% |
| | Left fore and hind | Male | 0 | Normal |
| Compound 1 (sodium salt) (20 mg/kg) | Whole | Female | 0 | Normal |
| | White | Female | 0 | Normal |
| | Left fore | Female | 0 | Normal |
| | Whole | Male | 0 | Normal |
| | White | Male | 0 | Normal |
| | Left fore | Male | 0 | Normal |
| Compound 81 as contrast (20 mg/kg) | Right fore | Female | 0 | Normal |
| | Left hind | Female | 0 | Normal |
| | Right hind | Female | 1 | Ulcer bleeding, injury area <25% |
| | Right fore | Male | 4 | Esophageal perforation |
| | Left hind | Male | 0 | Normal |
| | Right hind | Male | 0 | Normal |
| Compound 6 (sodium salt) (20 mg/kg) | Head | Female | 4 | Esophageal perforation |
| | Back | Female | 2 | Ulcer bleeding, injury area<50% |
| | Tail | Female | 1 | Ulcer bleeding, injury area<25% |

TABLE 7-continued

Injury status for different groups administered with drugs

| Group | Mark | Gender | Esophagus injury score | Injury status |
|---|---|---|---|---|
| | Head | Male | 3 | Ulcer bleeding, injury area<75% |
| | Back | Male | 4 | Esophageal perforation |
| | Tail | Male | 4 | Bleeding in a large area of esophageal wall, injury area >75% |

4. Conclusion

In comparison with the model group, the group of Compound 1 of the present invention shows a significant decrease of esophagitis index (P<0.01), which indicates Compound 1 of the present invention has good protection effects on esophagus; when comparing the group of the Compound 81 as contrast, and the group of Compound 6 of the present invention to the solvent group, P>0.05, showing no statistical significance, which indicate Compound 81 as contrast and Compound 6 of the present invention has no protection effect on reflux esophagitis in rats.

Experimental Example 3

In Vivo Pharmacokinetic Test of the Compounds of the Present Invention in Rats

1. Experimental Materials

Experimental animals: male Wistar rats, 6 rats/compound, body weight 180-220 g, purchased from Shandong University, certificate no.: SCXK (鲁) 20090001.

Experimental samples: Compound 1, Compound 29 and Compound 30 of the present invention, each of them is prepared according to the methods of the above examples, and dissolved in physiological saline before test.

2. Experimental Methods

Administration: as for intravenous push (I.V), Compound 1, Compound 29, Compound 30 were administered in a dose of 5 mg/kg, and a volume of 2 mL/kg; as for intragastric administration (P.O), Compound 1, Compound 29, Compound 30 were administered in a dose of 5 mg/kg, and a volume of 2 mL/kg. The rats were fasted without water deprivation for 12 before administration, and fed after 4 hours from the administration.

Blood collection: 0 h, 0.083 h, 0.25 h, 0.5 h, 1 h, 2 h, 4 h, 8 h, 24 h, at each time point, about 150 μL of whole blood was collected, centrifuged at 4° C. and 8000 rpm for 6 min using a low-temperature high-speed centrifuge, the separated plasma was frozen and stored at −80° C. in a refrigerator.

Analysis of plasma samples: as for Compound 1, Compound 29, Compound 30, 50 μL of plasma was taken, added with 120 μL internal standard solution (Tolbutamide, 5 ng/mL MeOH solution), subjected to 1500 rpm vortex for 2 min, then centrifuged at 14000 rpm for 5 min, the supernatant was collected, and analyzed by using LC-MS/MS.

Calculation formula: absolute bioavailability F %=[AUC]$_{INF(PO)}$*Dose$_{(IV)}$/[AUC]$_{INF(IV)}$*Dose$_{(PO)}$ 3. Experimental Results The Experimental results are shown in Table 8 and Table 9.

TABLE 8

PK evaluation results of the compound of the present invention in rats (P.O)

| Compound # | Dose (mg/kg) | AUC$_{inf}$ (ng/mL/h) | C$_{max}$ (ng/mL) | T$_{max}$ (h) | F % | CL (L/kg/h) |
|---|---|---|---|---|---|---|
| Compound 1 (sodium salt) | 5 | 676.867 | 1863.333 | 0.083-0.25 | 26.201 | — |
| Compound 29 | 5 | 1738.366 | 5776.667 | 0.083 | 49.161 | 3.22567 |
| Compound 30 (sodium salt) | 5 | 1263.547 | 3253.333 | 0.083-0.25 | 39.282 | 5.00967 |

TABLE 9

PK evaluation results of the compound of the present invention (I.V) in rats

| Compound # | Dose (mg/kg) | CL (L/kg/h) | Vss (L/kg) | T½ (h) |
|---|---|---|---|---|
| Compound 1 (sodium salt) | 5 | 1.950 | 0.255 | 0.172 |
| Compound 29 | 5 | 1.281 | 0.289 | 0.223 |
| Compound 30 (sodium salt) | 5 | 1.591 | 0.394 | 0.275 |

Wherein, AUC$_{INF}$ represents area under drug-time curve$_{0\to\infty}$; C$_{max}$ represents peak drug concentration in blood; T$_{max}$ represents a time for reaching peak drug concentration in blood; F % represents absolute bioavailability; CL represents clearance rate; Vss represents apparent volume of distribution; T$_{1/2}$ represents half-life period.

4. Conclusion

It can be seen from Table 8 and Table 9, the Compounds 1, 29 and 30 have good in vivo pharmacokinetic properties.

Preparation Examples

Manufacture of Enteric Coated Tablet of the Compound of the Present Invention

Tablet Core Formula:

| Name | Formula 1 | Formula 2 | Formula 3 | Formula 4 | Formula 5 |
|---|---|---|---|---|---|
| Compound 30 sodium salt (in C$_{20}$H$_{23}$N$_3$O$_4$S) | 10 g | 10 g | 10 g | 10 g | 10 g |
| Magnesium oxide | 5.0 g | 10 g | 30 g | 50 g | 70 g |
| Starch | 20 g | 15 g | — | 35 g | — |
| Mannitol | 35 g | 35 g | 35 g | — | 15 g |
| Cross-linked carboxymethylcellulose sodium | 15 g | — | — | — | — |

-continued

| Name | Formula 1 | Formula 2 | Formula 3 | Formula 4 | Formula 5 |
|---|---|---|---|---|---|
| Cross-linked povidone (XL-10) | — | 15 | 15 g | 5 g | — |
| 5% (w/w) povidone K30 anhydrous ethanol solution | 42 g | 45 g | 51 g | 58 g | 60 g |
| Cross-linked povidone (XL-10) (extra added) | — | — | 10 g | 15 g | 20 g |
| Magnesium stearate | 1% | 1% | 1% | 1% | 1% |
| Processed to form | 1000 tablets | 1000 tablets | 1000 tablets | 1000 tablets | 1000 tablets |

Formula of Isolation Coating:

| Component | Mass percentage |
|---|---|
| Gastric film coating premix (17B68966) | 7.5% |
| Ethanol | 77.9% |
| Purified water | 14.6% |

Formula of Enteric Coating:

| Components | Mass percentage |
|---|---|
| Enteric film coating premix (94O680000) | 7.6% |
| Ethanol | 92.4% |

Manufacture Method:

(1) providing Compound 30 sodium salt and mannitol, separately pulverizing, passing sieve, for standby use;

(2) weighing the pulverized Compound 30 sodium salt and magnesium oxide according to the formulation, mixing and passing sieve;

(3) weighing mannitol and cross-linked povidone (XL-10) or cross-linked carboxymethylcellulose sodium according to the formulation, mixing uniformly, adding with 5% (w/w) povidone K30 in anhydrous ethanol solution, forming a soft stuff, processing to form wet granules;

(4) drying the wet granules;

(5) trimming;

(6) fanally mixing, adding magnesium stearate and cross-linked povidone (XL-10), mixing uniformly;

(7) inspecting semi-finished product;

(8) tabletting;

(9) drying tablet core;

(10) coating an isolation coat;

(11) coating enteric coat;

(12) drying finished product, and packaging.

What is claimed is:

1. A compound of Formula (I), or a stereoisomer, solvate or pharmaceutically acceptable salt thereof:

wherein, $R^1$, $R^2$ and $R^3$ are independently hydrogen atom, $C_{1-4}$ alkyl, $C_{1-4}$ alkoxyl, $C_{1-4}$alkoxyl-$C_{1-4}$ alkyl, $C_{1-4}$alkoxyl-$C_{1-4}$ alkoxyl, halo$C_{1-4}$ alkyl or halo $C_{1-4}$ alkoxyl;

$R^4$ is hydrogen atom;

$R^5$ represents formula $R^6$ and $R^7$ are independently a hydrogen atom;

Ring A is a 5-membered ring having one oxygen atom;

Ring B is a 5-membered ring having one oxygen atom; and n is 1 or 2.

2. The compound of claim 1, or a stereoisomer, solvate or pharmaceutically acceptable salt thereof, wherein $R^1$, $R^2$ and $R^3$ are independently hydrogen atom, methyl, ethyl, methoxyl, ethoxyl, methoxylmethoxyl, 2-methoxylethoxyl, 3-methoxylpropoxy, ethoxylmethoxyl, 2-ethoxylethoxyl, 3-ethoxylpropoxy, propoxymethoxyl, difluoromethyl, trifluoromethyl, difluoromethoxyl, trifluoromethoxyl, 2,2-difluoroethoxyl or 2,2,2-trifluoroethoxyl;

$R^4$ is hydrogen atom; and $R^5$ represents

-continued

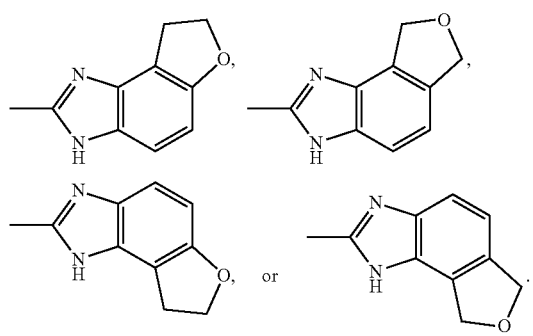

3. The compound of claim 2, or a stereoisomer, solvate or pharmaceutically acceptable salt thereof, wherein $R^1$ is hydrogen atom, methyl or methoxyl;
$R^2$ is methoxyl, 3-methoxylpropoxy or 2,2,2-trifluoroethoxyl;
$R^3$ is hydrogen atom, methyl or methoxyl;
$R^4$ is hydrogen atom; and
$R^5$ represents

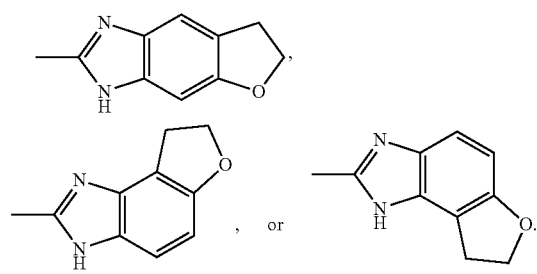

-continued

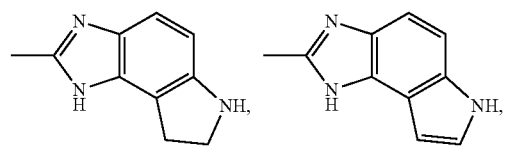

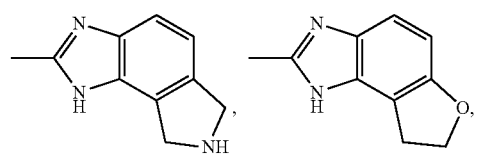

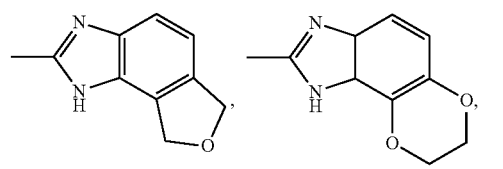

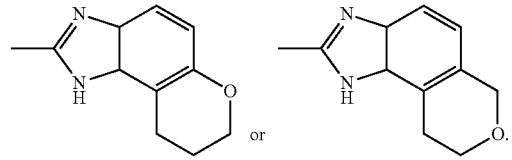

or

4. The compound of claim 3, or a stereoisomer, solvate or pharmaceutically acceptable salt thereof, wherein $R^1$ is methyl or methoxyl;
$R^2$ is methoxyl, 3-methoxylpropoxy or 2,2,2-trifluoroethoxyl;
$R^3$ is hydrogen atom or methyl;
$R^4$ is hydrogen atom; and
$R^5$ represents

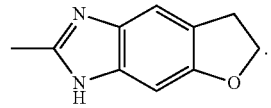

5. The compound of claim 1, or a stereoisomer, solvate or pharmaceutically acceptable salt thereof, wherein the compound is selected from:

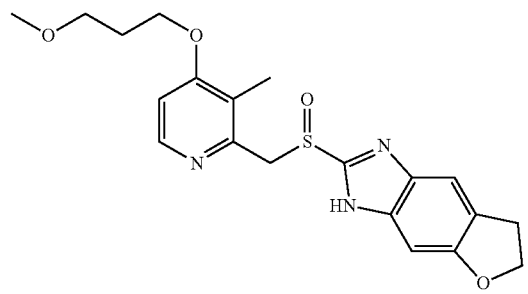 [SMILES: COCCCOc1ccnc(CS(=O)c2nc3cc4c(cc3[nH]2)OCC4)c1C]

2-[[4-(3-methoxylpropoxy)-3-methylpyridin-2-yl]methylsulfinyl]-6,7-dihydro-3H-benzofuro[5,6-d]imidazole,

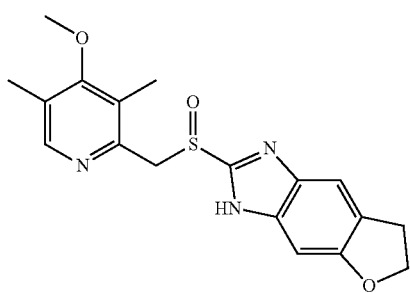 [SMILES: COc1c(C)cnc(CS(=O)c2nc3cc4c(cc3[nH]2)OCC4)c1C]

2-[(4-methoxyl-3,5-dimethylpyridin-2-yl)methylsulfinyl]-6,7-dihydro-3H-benzofuro[5,6-d]imidazole,

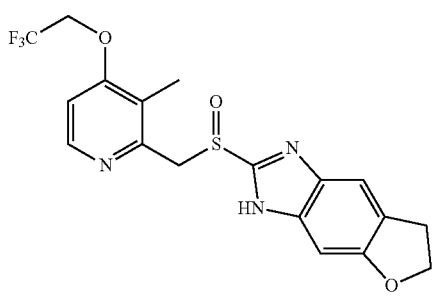 [SMILES: Cc1c(OCC(F)(F)F)ccnc1CS(=O)c1nc2cc3c(cc2[nH]1)OCC3]

2-[[3-methyl-4-(2,2,2-trifluoroethoxyl)pyridin-2-yl]methylsulfinyl]-6,7-dihydro-3H-benzofuro[5,6-d]imidazole, and

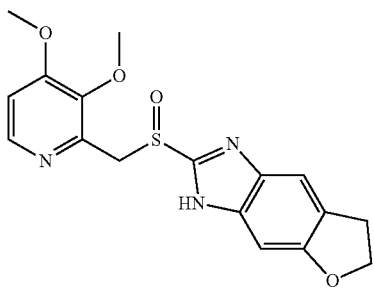 [SMILES: COc1ccnc(CS(=O)c2nc3cc4c(cc3[nH]2)OCC4)c1OC]

2-[(3,4-dimethoxylpyridin-2-yl)methylsulfinyl]-6,7-dihydro-3H-benzofuro[5,6-d]imidazole.

6. The compound of claim 1, or a pharmaceutically acceptable salt thereof, wherein the compound has a structure of the following formula:

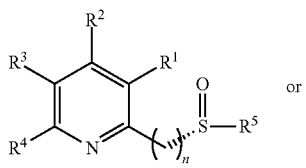

(I-1)

or

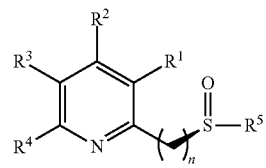

(I-2)

wherein, $R^1$, $R^2$, $R^3$, $R^4$, $R^5$ and n have the meanings as defined in claim 1.

7. The compound of claim 6, or a pharmaceutically acceptable salt thereof, wherein a) $R^1$, $R^2$ and $R^3$ are independently hydrogen atom, $C_{1-4}$ alkyl, $C_{1-4}$ alkoxyl, $C_{1-4}$alkoxyl-$C_{1-4}$ alkyl, $C_{1-4}$alkoxyl-$C_{1-4}$ alkoxyl, halo$C_{1-4}$ alkyl or halo$C_{1-4}$ alkoxyl;
$R^4$ is hydrogen atom;
$R^5$ represents formula

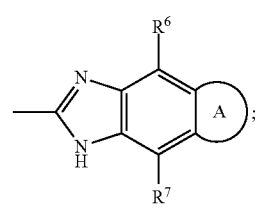

$R^6$ and $R^7$ are independently hydrogen atom;
Ring A is a 5-membered ring having one oxygen atom; or b) $R^1$ is $C_{1-4}$ alkyl or halo$C_{1-4}$ alkyl;
$R^2$ is $C_{1-4}$ alkoxyl, $C_{1-4}$ alkoxyl-$C_{1-4}$ alkyl, $C_{1-4}$alkoxyl-$C_{1-4}$ alkoxyl or halo$C_{1-4}$ alkoxyl;
$R^3$ and $R^4$ are independently hydrogen atom;
$R^5$ represents formula

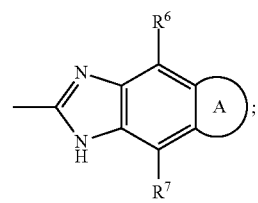

$R^6$ and $R^7$ are independently hydrogen atom;
Ring A is a 5-membered ring having one oxygen atom; or c) wherein the compound is

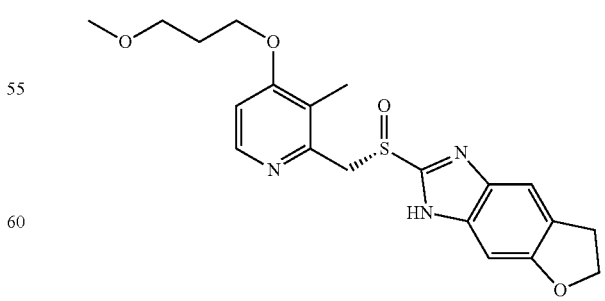

(S)-2-[[[4-(3-methoxylpropoxy)-3-methyl-2-pyridyl]methyl]sulfinyl]-6,7-dihydro-3H-benzofuro[5,6-d]imidazole, or

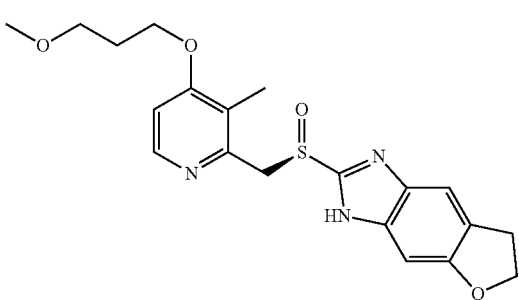

(R)-2-[[[4-(3-methoxylpropoxy)-3-methyl-2-pyridyl]methyl]sulfinyl]-6,7-dihydro-3H-benzofuro[5,6-d]imidazole.

8. A pharmaceutical composition comprising an effective amount of a compound according to claim 1, or a stereoisomer, solvate or pharmaceutically acceptable salt thereof, and a pharmaceutically acceptable excipient.

9. A method for preparing a compound of claim 1, the method comprising: performing a substitution reaction of a compound of Formula (II) and a compound of Formula (III) to form a compound of Formula (I'), and converting the Formula (I') in the presence of m-chloro-peroxybenzoic acid to obtain a compound of Formula (I),

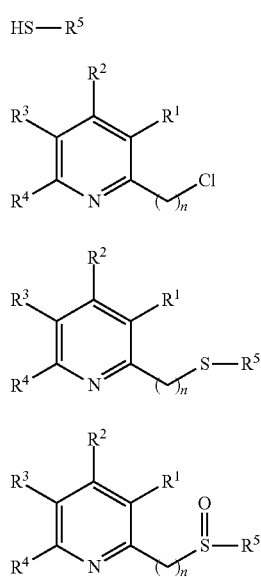

wherein, $R^1$, $R^2$, $R^3$, $R^4$, $R^5$ and n have the meanings as defined in claim 1.

10. A method for preparing a compound of claim 7 options a) and b), the method comprising: adding the compound of Formula (I') to a chiral separating agent to obtain the desired compound.

11. A method of treatment of a patient comprising the step of administering the compound of claim 1, or a stereoisomer, solvate or pharmaceutically acceptable salt thereof for treatment of peptic ulcer, ulcer hemorrhage and diseases associated with gastric acid.

12. The compound of claim 1, or a stereoisomer, solvate or pharmaceutically acceptable salt thereof, wherein $R^1$ is $C_{1-4}$ alkyl or haloC$_{1-4}$ alkyl;
$R^2$ is $C_{1-4}$ alkoxyl, $C_{1-4}$alkoxyl-$C_{1-4}$ alkyl, $C_{1-4}$alkoxyl-$C_{1-4}$ alkoxyl or haloC$_{1-4}$ alkoxyl;
$R^3$ and $R^4$ are independently hydrogen atom;
$R^5$ represents formula

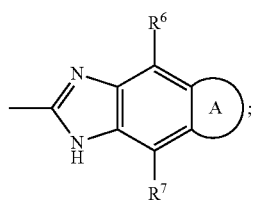

$R^6$ and $R^7$ are independently hydrogen atom; and
Ring A is a 5-membered ring having one oxygen atom.

13. The compound of claim 1, or a stereoisomer, solvate or pharmaceutically acceptable salt thereof, wherein
$R^1$, $R^2$ and $R^3$ are independently hydrogen atom, methyl, ethyl, methoxyl, ethoxyl, methoxylmethoxyl, 2-methoxylethoxyl, 3-methoxylpropoxy, ethoxylmethoxyl, 2-ethoxylethoxyl, 3-ethoxylpropoxy, propoxymethoxyl, difluoromethyl, trifluoromethyl, difluoromethoxyl, trifluoromethoxyl, 2,2-difluoroethoxyl or 2,2,2-trifluoroethoxyl;
$R^4$ is hydrogen atom; and
$R^5$ represents

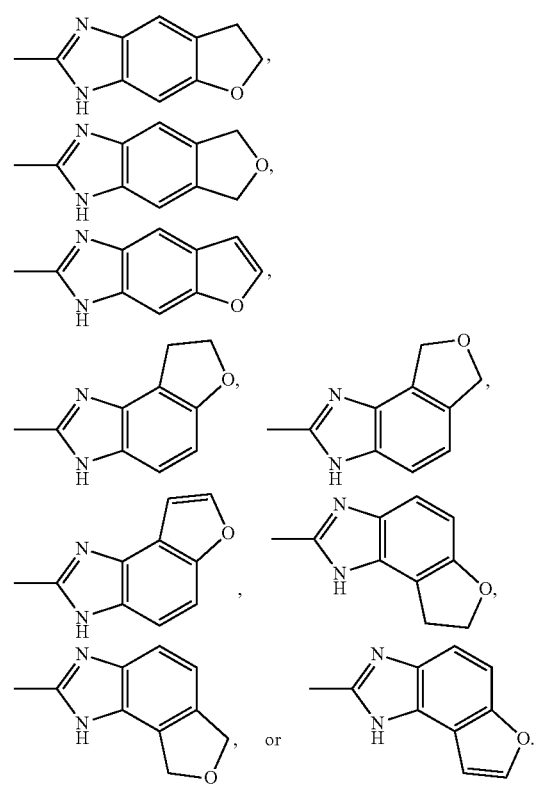

* * * * *